US012126995B2

(12) United States Patent
Hua et al.

(10) Patent No.: US 12,126,995 B2
(45) Date of Patent: Oct. 22, 2024

(54) SECURED COMMUNICATIONS IN MEDICAL MONITORING SYSTEMS

(71) Applicant: ABBOTT DIABETES CARE INC., Alameda, CA (US)

(72) Inventors: Xuandong Hua, Mountain View, CA (US); Kurt E. Leno, San Leandro, CA (US); Tony S. Lee, Alameda, CA (US); Kevin M. Ow-Wing, Castro Valley, CA (US); Danny Chan, Daly City, CA (US); Victor Paishi Huang, Union City, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 0 days.

(21) Appl. No.: 17/464,271

(22) Filed: Sep. 1, 2021

(65) Prior Publication Data

US 2022/0070666 A1   Mar. 3, 2022

Related U.S. Application Data

(63) Continuation of application No. PCT/US2021/048512, filed on Aug. 31, 2021.
(Continued)

(51) Int. Cl.
*H04W 12/03* (2021.01)
*G16H 40/67* (2018.01)
(Continued)

(52) U.S. Cl.
CPC .......... *H04W 12/037* (2021.01); *G16H 40/67* (2018.01); *H04L 9/0618* (2013.01); *H04L 9/065* (2013.01); *H04L 9/3271* (2013.01)

(58) Field of Classification Search
CPC . H04W 12/037; H04W 12/033; H04W 12/06; G16H 40/67; G16H 40/63;
(Continued)

(56) References Cited

U.S. PATENT DOCUMENTS 4,561,443 A   12/1985  Hogrefe et al.
5,390,671 A    2/1995  Lord et al.
(Continued)

FOREIGN PATENT DOCUMENTS

EP   2 407 094        1/2012
EP   3 158 922 A1     4/2017
(Continued)

OTHER PUBLICATIONS

Lara, el al. "A Lightweight Cipher Based on Salsa20 for Resource-Constrained IoT Devices" 2018, Sensors 18, No. 10: 3326. https://doi.org/10.3390/s18103326, pp. 1-15 (Year: 2018).*
(Continued)

*Primary Examiner* — Harunur Rashid
(74) *Attorney, Agent, or Firm* — Baker Botts L.L.P.

(57) ABSTRACT

In one embodiment, a method for secured communication between a medical sensor and a computing device includes receiving, by the medical sensor, an authentication request from the computing device. The method includes generating, based on values provided in the authentication request, a challenge-response message for the computing device. The method includes receiving, from the computing device, a responsive challenge-response message. The method includes verifying that the responsive challenge-response message includes an expected value and corresponds to an expected format. The method includes, in response to verifying the responsive challenge-response message, sending a sensor secret value to the computing device.

7 Claims, 12 Drawing Sheets

Related U.S. Application Data

(60) Provisional application No. 63/072,647, filed on Aug. 31, 2020.

(51) Int. Cl.
*H04L 9/06* (2006.01)
*H04L 9/32* (2006.01)
*H04W 12/037* (2021.01)

(58) Field of Classification Search
CPC ..... H04L 9/0618; H04L 9/065; H04L 9/3271; H04L 9/0866; H04L 9/3213; H04L 9/3273; H04L 2209/24; H04L 2209/805; H04L 2209/88; H04L 63/0869
See application file for complete search history.

(56) References Cited

U.S. PATENT DOCUMENTS

| | | | |
|---|---|---|---|
| 5,482,473 | A | 1/1996 | Lord et al. |
| 5,660,163 | A | 8/1997 | Schulman et al. |
| 5,690,119 | A | 11/1997 | Rytky et al. |
| 6,096,268 | A | 8/2000 | Inbar |
| 6,159,181 | A | 12/2000 | Crossman et al. |
| 6,175,752 | B1 | 1/2001 | Say et al. |
| 6,266,551 | B1 | 7/2001 | Osadchy et al. |
| 6,293,925 | B1 | 9/2001 | Safabash et al. |
| 6,298,255 | B1 | 10/2001 | Cordero et al. |
| 6,560,471 | B1 | 5/2003 | Heller et al. |
| 6,565,509 | B1 | 5/2003 | Plante et al. |
| 6,689,056 | B1 | 2/2004 | Kilcoyne et al. |
| 6,695,860 | B1 | 2/2004 | Ward et al. |
| 7,344,500 | B2 | 3/2008 | Talbot et al. |
| 7,693,485 | B2 | 4/2010 | Parys |
| 9,000,914 | B2 | 4/2015 | Baker et al. |
| 9,211,065 | B2 | 12/2015 | Marsh et al. |
| 9,344,777 | B2 | 5/2016 | He et al. |
| 9,824,691 | B1* | 11/2017 | Montero ............... G10L 15/26 |
| 9,980,140 | B1 | 5/2018 | Spencer et al. |
| 10,375,222 | B2 | 8/2019 | Mandapaka et al. |
| 2002/0109621 | A1 | 8/2002 | Khair et al. |
| 2003/0100821 | A1 | 5/2003 | Heller et al. |
| 2003/0144581 | A1 | 7/2003 | Conn et al. |
| 2003/0153900 | A1 | 8/2003 | Aceti et al. |
| 2004/0106860 | A1 | 6/2004 | Say et al. |
| 2004/0117204 | A1 | 6/2004 | Mazar et al. |
| 2004/0122353 | A1 | 6/2004 | Shahmirian et al. |
| 2004/0127958 | A1 | 7/2004 | Mazar et al. |
| 2004/0133164 | A1 | 7/2004 | Funderburk et al. |
| 2005/0027463 | A1 | 2/2005 | Goode, Jr. et al. |
| 2005/0049501 | A1 | 3/2005 | Conero et al. |
| 2005/0177398 | A1 | 8/2005 | Watanabe et al. |
| 2005/0204134 | A1 | 9/2005 | Von Arx et al. |
| 2005/0240245 | A1 | 10/2005 | Bange et al. |
| 2005/0242479 | A1 | 11/2005 | Petisce et al. |
| 2005/0261563 | A1 | 11/2005 | Zhou et al. |
| 2005/0283114 | A1 | 12/2005 | Bresina et al. |
| 2006/0016700 | A1 | 1/2006 | Brister et al. |
| 2006/0025663 | A1 | 2/2006 | Talbot et al. |
| 2006/0081469 | A1 | 4/2006 | Lee |
| 2007/0038044 | A1 | 2/2007 | Dobbles et al. |
| 2007/0043279 | A1 | 2/2007 | Mannheimer et al. |
| 2007/0060801 | A1 | 3/2007 | Neinast |
| 2007/0073129 | A1 | 3/2007 | Shah et al. |
| 2007/0173710 | A1 | 7/2007 | Petisce et al. |
| 2007/0219480 | A1 | 9/2007 | Kamen et al. |
| 2007/0288265 | A1 | 12/2007 | Quinian et al. |
| 2008/0009805 | A1 | 1/2008 | Ethelfeld |
| 2008/0097246 | A1 | 4/2008 | Stafford |
| 2008/0129486 | A1 | 6/2008 | Jeckelmann et al. |
| 2008/0269687 | A1 | 10/2008 | Chong et al. |
| 2008/0275313 | A1 | 11/2008 | Brister et al. |
| 2008/0278333 | A1 | 11/2008 | Fennell et al. |
| 2008/0300476 | A1 | 12/2008 | Stafford |
| 2008/0312512 | A1 | 12/2008 | Brukalo et al. |
| 2008/0319414 | A1 | 12/2008 | Yodfat et al. |
| 2010/0045425 | A1 | 2/2010 | Chivallier |
| 2010/0230285 | A1 | 9/2010 | Hoss et al. |
| 2010/0302979 | A1 | 12/2010 | Reunamäki |
| 2010/0327063 | A1 | 12/2010 | Medina et al. |
| 2011/0103583 | A1* | 5/2011 | Yoon ................... H04L 9/3093 380/255 |
| 2011/0125000 | A1 | 5/2011 | Rantala |
| 2011/0177780 | A1 | 7/2011 | Sato et al. |
| 2011/0213225 | A1 | 9/2011 | Bernstein et al. |
| 2011/0282671 | A1 | 11/2011 | Dicks et al. |
| 2012/0123227 | A1 | 5/2012 | Sun et al. |
| 2012/0182917 | A1 | 7/2012 | Edlund |
| 2012/0237022 | A1 | 9/2012 | Berson et al. |
| 2012/0255875 | A1 | 10/2012 | Vicente et al. |
| 2012/0260323 | A1 | 10/2012 | San Vicente et al. |
| 2012/0265035 | A1 | 10/2012 | Bohm et al. |
| 2013/0078912 | A1 | 3/2013 | San Vicente et al. |
| 2013/0310896 | A1 | 11/2013 | Mass |
| 2014/0266776 | A1 | 9/2014 | Miller et al. |
| 2014/0266785 | A1 | 9/2014 | Miller et al. |
| 2014/0273858 | A1 | 9/2014 | Panther et al. |
| 2014/0313052 | A1 | 10/2014 | Yarger et al. |
| 2014/0379273 | A1 | 12/2014 | Petisce et al. |
| 2015/0038818 | A1 | 2/2015 | Cole |
| 2015/0089222 | A1 | 3/2015 | White et al. |
| 2015/0118658 | A1 | 4/2015 | Mayou et al. |
| 2015/0123810 | A1 | 5/2015 | Hernandez-Rosas et al. |
| 2015/0205947 | A1 | 7/2015 | Berman et al. |
| 2015/0207796 | A1 | 7/2015 | Love et al. |
| 2015/0289124 | A1 | 10/2015 | Palin et al. |
| 2016/0210099 | A1 | 7/2016 | Hampapuram et al. |
| 2016/0234020 | A1 | 8/2016 | Nix |
| 2017/0149567 | A1* | 5/2017 | Moskal ............... G06F 21/64 |
| 2017/0180341 | A1* | 6/2017 | Walker ............... H04L 9/3242 |
| 2019/0042249 | A1* | 2/2019 | Suresh ............... G06F 9/30036 |
| 2019/0089533 | A1* | 3/2019 | Agnello ............... G06F 21/45 |
| 2020/0029842 | A1* | 1/2020 | Felix ............... G06F 21/6218 |
| 2021/0048512 | A1* | 2/2021 | Che ............... G01S 7/4808 |

FOREIGN PATENT DOCUMENTS

| | | |
|---|---|---|
| JP | WO2015/194381 A1 | 12/2015 |
| WO | WO 99/58190 | 11/1999 |
| WO | WO 02/15778 | 2/2002 |
| WO | WO 03/026728 | 4/2003 |
| WO | WO 2004/006982 | 1/2004 |
| WO | WO 2005/018450 | 3/2005 |
| WO | WO 2005/046780 | 5/2005 |
| WO | WO 2006/040083 | 4/2006 |
| WO | WO 2006/094513 | 9/2006 |
| WO | WO 2006/121921 | 11/2006 |
| WO | WO 2007/002189 A2 | 1/2007 |
| WO | WO 2007/097754 | 8/2007 |
| WO | WO 2008/065646 | 6/2008 |
| WO | WO 2008/073813 | 6/2008 |
| WO | WO 2008/114223 | 9/2008 |
| WO | WO 2008/115409 | 9/2008 |
| WO | WO 2008/157821 | 12/2008 |
| WO | WO 2009/007287 | 1/2009 |
| WO | WO 2009/035773 | 3/2009 |
| WO | WO 2009/039013 | 3/2009 |
| WO | WO 2013/044153 A1 | 3/2013 |
| WO | WO 2013/090731 A1 | 6/2013 |
| WO | WO 2014/011488 A2 | 1/2014 |
| WO | WO 2014/179343 A1 | 11/2014 |
| WO | WO 2015/069797 A1 | 5/2015 |
| WO | WO 2016/092448 A1 | 6/2016 |
| WO | WO 2017/172781 A1 | 10/2017 |
| WO | WO 2018/075333 A2 | 4/2018 |

OTHER PUBLICATIONS

Li el al., "A Framework for Qualitative Communications Using Big Packet Protocol" Aug. 14, 2019, NEAT'19: Proceedings of the ACM SIGCOMM 2019 Workshop on Networking for Emerging

(56) References Cited

OTHER PUBLICATIONS

Applications and Technologies, Aug. 2019 pp. 22-28, https://doi.org/10.1145/3341558.3342201 (Year: 2019).*
Bluetooth Specification, Encryption and Authentication Overview, vol. 6, Version 4.0, 1 page (2010).
Cunningham et al., "In Vivo Glucose Sensing," Wiley & Sons (2010).
Cornelius, "Usable Security for Wireless Body-Area Networks," Dartmouth College PhD Dissertations. 42 (2013).
Diallo et al., "A Secure Authentication Scheme for Bluetooth Connection," 5th International Conference on Computer & Communication Engineering, DOI 10.1109/ICCCE.2014.29, 60-63 (2014).
Ellmerer et al., "Measurement of interstitial albumin in human skeletal muscle and adipose tissue by open-flow microperfusion," Am. J. Physiol. Endocrinol. Metab., 278: E352-E356 (2000).
Finkenzeller, "RFID Handbook: Fundamentals and Applications in Contactless Smart Cards, Radio Frequency Identification and Near-Field Communication", Third Edition, 4 pages (2010).
German Infringement Complaint (2021) with English Abstract.
German Infringement Complaint Service addressed to Dexcom Deutschland GmbH (2021).
Gomez et al., "Overview and Evaluation of Bluetooth Low Energy: An Emerging Low-Power Wireless Technology," Sensors, 12, 11734-11753 (2012).
Guder et al., "Samples: From the Patient to the Laboratory, The impact of preanalytical variables on the quality of laboratory results," Wiley-Vch GmbH & Co. KGaA (2003).
Higson et al., "Biosensors: a viable monitoring technology?" Med. & Biol. Eng. & Comput., 32, 601-609 (1994).
Mohanty et al., Biosensors: A tutorial review, IEEE Potentials, 35-40 (2006).
Near Field Communication (NFC) Technology and Measurements, White Paper, Rohde & Schwarz, 18 pages (2011).
Near Field Communication (NFC) Technology and Measurements, White Paper, Rohde & Schwarz, 1 page (2011).
Padgette et al., "Guide to Bluetooth Security, Recommendations of the National Institute of Standards and Technology," NIST, U.S. Dept. of Commerce, Special Publication 800-121 Revision 1 (2012).
Rivest et al., "A Method for Obtaining Digital Signatures and Public-Key Cryptosystems," MIT, 15 pages (1977).
Schaupp et al., "Direct access to interstitial fluid in adipose tissue in humans by use of open-flow microperfusion," E401-E408, Downloaded from journals.physiology.org/journal/ajpendo (092.040.147.197) on Oct. 4, 2021.
Seymour et al., Bluetooth Master/Slave Communications and Sniff/Sniff Sub-rating Modes White Paper, Aug. 14, 2008.
Sola-Gazagnes, et al., "Emergent technologies applied to diabetes: What do we need to integrate continuous glucose monitoring into daily practice? Where the long-term use of continuous glucose monitoring stands in 2011", Diabetes & Metabolism, vol. 37, pp. S65-S70 (2011).
Specification of the Bluetooth System, Experience More, Master Table of Contents & Compliance Requirements vol. 0, Covered Core Package Version: 4.0, 2302 pages (2010).
Specification of the Bluetooth System, Experience More, Specification vol. 0, Covered Core Package Version: 4.0, 89 pages (2010).
Specification of the Bluetooth System, Master Table of Contents & Compliance Requirements, Version 4.1 (2013).
Specification of the Bluetooth System, Master Table of Contents & Compliance Requirements, Version 4.2 (2014).
Stallings, "Cryptography and Network Security, Principles and Practice," 5th Ed., Prentice Hall (2011).
Strickland, Ray, et al., "Continuous Glucose Monitoring Profile Bluetooth® Profile Specification," Interest Group, v1.0.1 (2015).
The New Shorter Oxford English Dictionary, p. 50.
Townsend et al., "Getting Started with Bluetooth Low Energy," O'Reilly (2014).
Wikipedia, "Analyte" retrieved from https://en.wikipedia.org/w/index.php?title=Analyte&oldid=527866671 (2012).
Wikipedia, "Bluetooth", 25 pages retrieved from https://en.wikipedia.org/wiki/Bluetooth (2022).
Wikipedia, Bluetooth Low Energy, 11 pages retrieved from https://en.wikipedia.org/wiki/Bluetooth_Low Energy (2022).
Wikipedia, Challenge-response authentication retrieved from https://en.wikipedia.org/wiki/Challenge%E2%80%93response_authentication (2013).
Wikipedia, Digital Signature, 10 pages retrieved from https://en.wikipedia.org/wiki/Digital_signature (2021).
Wikipedia, Digital Signature, 10 pages (2012).
Wikipedia, "In vivo" retrieved from https://en.wikipedia.org/w/index.php?title=In_vivo&oldid=524960105 (2012).
Wikipedia, "Near-field communication" retrieved from https://en.wikipedia.org/w/index.php?title=Near-field_communication&oldid=525308529 (2012).
Wikipedia, RSA (cryptosystem), 17 pages retrieved from https://en.wikipedia.org/wiki/RSA_(cryptosystem) (2021).
U.S. Appl. No. 60/614,683, filed Sep. 30, 2004, Brister et al.
"Setting Your Sensor Settings" retrieved from "https://web.archive.org/web/20160803065621/http://www.medtronicdiabetes.com:80/customer-support/device-settings-and-features/sensor-settings/setting-sensor-settings" on Nov. 18, 2022, 5 pages.
Dexcom G5 Mobile Continuous Glucose Monitoring System, Advisory Committee Briefing Materials, Clinical Chemistry and Clinical Toxicology Devices Panel, 283 pages (2016).
Dowla, "The Basics of Radio Frequency Identification (RFID) Technology", Handbook of RF & Wireless Technologies, Chapter 14, 44 pages (2004).
Evans, et al., "Clinical temperature acquisition using proximity telemetry", J. Biomed. Eng., 13:83-86 (1991).
Finkenzeller, "RFID Handbook: Fundamentals and Applications in Contactless Smart Cards and Identification", Second Edition, 114 pages (2003).
Heller, et al., "Electrochemical Glucose Sensors and Their Applications in Diabetes Management", Chemical Reviews, 108(7):2482-2505 (2008).
Lee, "RFID Coil Design", Microchip Technology Inc., DS00678B, pp. 1-19 (1998).
Liang, et al., "An implantable bi-directional wireless transmission system for transcutaneous biological signal recording", Physiological Measurement, 26:83-97 (2005).
Radio Frequency Identification RFID, AIM Inc., White Paper, Document Version 1.2, 17 pages (2001).
Sorrells, "Passive RFID Basics", Microchip Technology Inc., DS00680B, pp. 1-5 (1998).
International Search Report and Written Opinion corresponding to International Patent Application No. PCT/US2021/048512 dated Jan. 18, 2022.
U.S. Appl. No. 60/587,787, filed Jul. 13, 2004, Brister, et al.
"Within Definition & Meaning" retrieved from "https://www.dictionary.com/browse/within" on Sep. 9, 2022, 5 pages.
Chuang et al., "Pilot Studies of Transdermal Continuous Glucose Measurement in Outpatient Diabetic Patients and in Patients during and after Cardiac Surgery," Journal of Diabetes Science and Technology, 595-602 (2008).
Exhibit B-22.pdf—Opponent's Written Response in Opposition of EP 3 730 045, Sep. 27, 2023, 43 pages.
McCartney et al., "In vivo glucose sensing for diabetes management: progress towards non-invasive monitoring," BMJ, vol. 319, 4 pages (1999).
Wang et al. "A Feasible IMD Communication Protocol: Security without Obscurity," School of Engineering and Computing Sciences, NYIT Research Experience for Undergraduates (REU), May 26-Jul. 30, 2015, 1 page.
U.S. Pat. No. 10,375,222, issued Aug. 6, 2019, 442 pages.
NFC Forum Bluetooth Special Interest Group, Bluetooth® Secure Simple Pairing Using NFC, 39 pages (2014).
Omre, "Bluetooth Low Energy: Wireless Connectivity for Medical Monitoring", Journal of Diabetes Science and Technology, vol. 4, No. 2, pp. 457-463 (2010).
Padgette, et al., "Guide to Bluetooth Security—Recommendations of the National Institute of Standards and Technology," National

(56) References Cited

OTHER PUBLICATIONS

Institute of Standards and Technology, U.S. Dept. of Commerce, 800-121, Rev 1, 48 pages (May 2017).

Specification vol. 0, Specification of the Bluetooth System, Experience More, Master Table of Contents & Compliance Requirements, 134 pages (2010).

Specification vol. 0, Specification of the Bluetooth System, Wireless connections made easy, Master Table of Contents & Compliance Requirements, 92 pages (2003).

Strömmer et al., "Application of Near Field Communication for Health Monitoring in Daily Life," Proceedings of the 28th IEEE, EMBS Annual International Conference, New York City, USA, Aug. 30-Sept. 3, 2006, pp. 3246-3249.

Zhang, et al., "Bluetooth Low Energy for Wearable Sensor-based Healthcare Systems", 2014 Health Innovations and Point-of-Care Technologies Conference, pp. 251-254 (2014).

\* cited by examiner

SECURED COMMUNICATIONS IN MEDICAL MONITORING SYSTEMS

PRIORITY

This application is a continuation of International Patent Application No. PCT/US21/48512, filed 31 Aug. 2021, which claims the benefit under 35 U.S.C. § 119(e) of U.S. Provisional Patent Application No. 63/072,647, filed 31 Aug. 2020, which is incorporated herein by reference.

BACKGROUND

The disclosed subject matter relates to securely exchanging data between medical devices with less computational capability or resources and other devices, including but not limited to personal computing devices, interface devices, remote servers, or other medical devices.

Certain medical devices can wirelessly transmit data to, and receive data from, other computing devices. While some of these medical devices are equipped with powerful processors and operate using a permanent power supply, other medical devices are designed to operate efficiently, using little power. Low-power medical devices can also have less computational capabilities or resources than devices to which these medical devices are communicating. In some cases, low-power devices can transmit or receive sensitive data, including, for example, a patient's private medical information. It can be challenging to protect the sensitive data from interception and tampering using less computational capabilities or resources typical of such low-power medical devices, which can include reduced capabilities of low-power medical devices to, for example, run encryption or decryption processes.

Active medical sensors are one example of medical devices for which wireless communication capabilities can be incorporated. Medical sensors can gather private medical information about a user. After collecting data, medical sensors can transfer the medical information to more powerful devices for data collection and analysis. Such features can involve the medical devices communicating data with other computing devices. Additionally or alternatively, some sensors can be physically connected with other devices to facilitate data transfer, either after removal from the patient or while still connected to the patient, which can restrict the patient's free movement. Wireless communication can be more convenient to allow communication without involving a physical connection to another device. A challenge of communicating such data is preventing interception by a third party. Data security can be desirable in the context medical devices, where intercepted data can include private details about the patient's health or medical history and other sensitive information. Furthermore, tampering or otherwise modifying the intercepted data or the operation of the device can result in incorrect medical information being provided to the user.

Medical sensors can be designed to be disposable and low cost, and such medical sensors can have less power or computational capabilities when executing data security algorithms for protecting wireless communications compared to other devices. Accordingly, there is an opportunity for methods and systems that can be implemented by low-power medical devices with less computational capabilities or resources to provide secure wireless communications and to facilitate transfer of data from such medical devices to other devices.

SUMMARY

The purpose and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims hereof, as well as from the drawings.

To achieve these and other advantages and in accordance with the purpose of the disclosed subject matter, as embodied and broadly described, the disclosed subject matter includes systems and method for a secured communication protocol for use by a medical sensor. Exemplary methods can include receiving by a medical sensor an activation signal from a computing device. The medical sensor can, in response to the activation signal, verify one or more authentication values associated with the computing device. In response to a successful verification, the medical sensor can begin to collect sensor information from a patient. As embodied herein, the sensor information can include medical data about the patient. As embodied herein, the medical sensor can receive the activation signal through a short-range communication protocol capable of delivering wireless power to one or more communication modules of the medical sensor. As embodied herein, the medical sensor can use information received through the short-range communication protocol to establish a connection with the computing device over a second short-range communication protocol without requiring additional verification from a user, including but not limited to the patient. As embodied herein, the short-range communication protocol can include Near-Field Communication (NFC) and the second short-range communication can include Bluetooth Low Energy (BLE). As embodied herein, the medical sensor can include less powerful computational resources than the computing device.

According to other aspects of the disclosed subject matter, systems and method can include receiving, by the medical sensor, an authentication request from a computing device. The medical sensor can use information included in the authentication request to generate a challenge response message for the computing device. The medical sensor can receive a responsive challenge response message from the computing device and can further verify that the responsive challenge response message corresponds to an expected format and value. The medical sensor can subsequently send a sensor secret to the computing device. As embodied herein, the sensor secret can include data unique to the medical sensor and random values. As embodied herein, the random value can be based on predefined values provided to the sensor, values generated by a communication module of the medical sensor, or values generated in response to user interactions. The medical sensor can encrypt one or more medical readings using an encryption key derived from the sensor secret using a first cryptographic function and send the encrypted medical readings to the computing device. As embodied herein, the encryption key can be used with a specialized low-power stream cipher or block cipher. The first cryptographic function can include performing add-rotate-xor operations on the medical readings. As embodied herein, the add-rotate-xor operations can include segmenting the unencrypted medical readings into a series of data blocks, segmenting each data block into more than one words, and performing a series of additional operations on each data block. The additional operations can include rotating bits of a first word of the more than one words of the block by a first fixed amount, adding a second word of the more than one words of the block, performing a bitwise xor operation of the first key into the first word, rotating bits of the second word by a second fixed amount, and performing a bitwise xor operation of the first word into the second word. As embodied herein, the medical readings can include body temperature, heart rate, blood glucose levels, motion, and other medical readings.

According to other aspects of the disclosed subject matter, systems and methods can include receiving, by a first computing device from a medical sensor, a set of medical readings encrypted using a first key derived from a sensor secret and a first encryption algorithm. The first encryption algorithm can include performing add-rotate-xor operations on the medical readings. The sensor secret can include unique values associated with the medical sensor and random values generated by the medical sensor. The methods can include deriving, by the computing device, the first key based on the sensor secret. The methods can include decrypting, by the computing device, the set of medical readings using the derived first key. The methods can include encrypting the decrypted medical readings using a second key and a second encryption algorithm. The second key can include information unique to the computing device and random values generated by the computing device. The second encryption algorithm can be different, and as embodied herein, can be a more computationally complex encryption algorithm than the first encryption algorithm. The methods can include transmitting the encrypted medical readings to a second computing device. As embodied herein, the encrypted medical readings can be transmitted to second computing device via wired or wireless communication. The encrypted medical readings can be transmitted using a packet-level-encoding computing protocol. As embodied herein, the methods can include the second computing device decrypting the encrypted medical readings and transmitting them to a third computing device after encrypting the medical readings with the third key and a third encryption algorithm, where the first key, second key, and third key are all different and derived from different root values and where the first encryption algorithm, second encryption algorithm, and third encryption algorithm are all different. As embodied herein, the medical sensor can include less powerful computational resources than the first computing device. The first computing device can include less powerful computational resources than the second computing device.

It is to be understood that both the foregoing general description and the following detailed description are exemplary and are intended to provide further explanation of the disclosed subject matter.

The accompanying drawings, which are incorporated in and constitute part of this specification, are included to illustrate and provide a further understanding of the methods and systems of the disclosed subject matter. Together with the description, the drawings explain the principles of the disclosed subject matter.

BRIEF DESCRIPTION OF THE DRAWINGS

The details of the subject matter set forth herein, both as to its structure and operation, may be apparent by study of the accompanying figures, in which like reference numerals refer to like parts.

DETAILED DESCRIPTION OF EXAMPLE EMBODIMENTS

Figure 1:
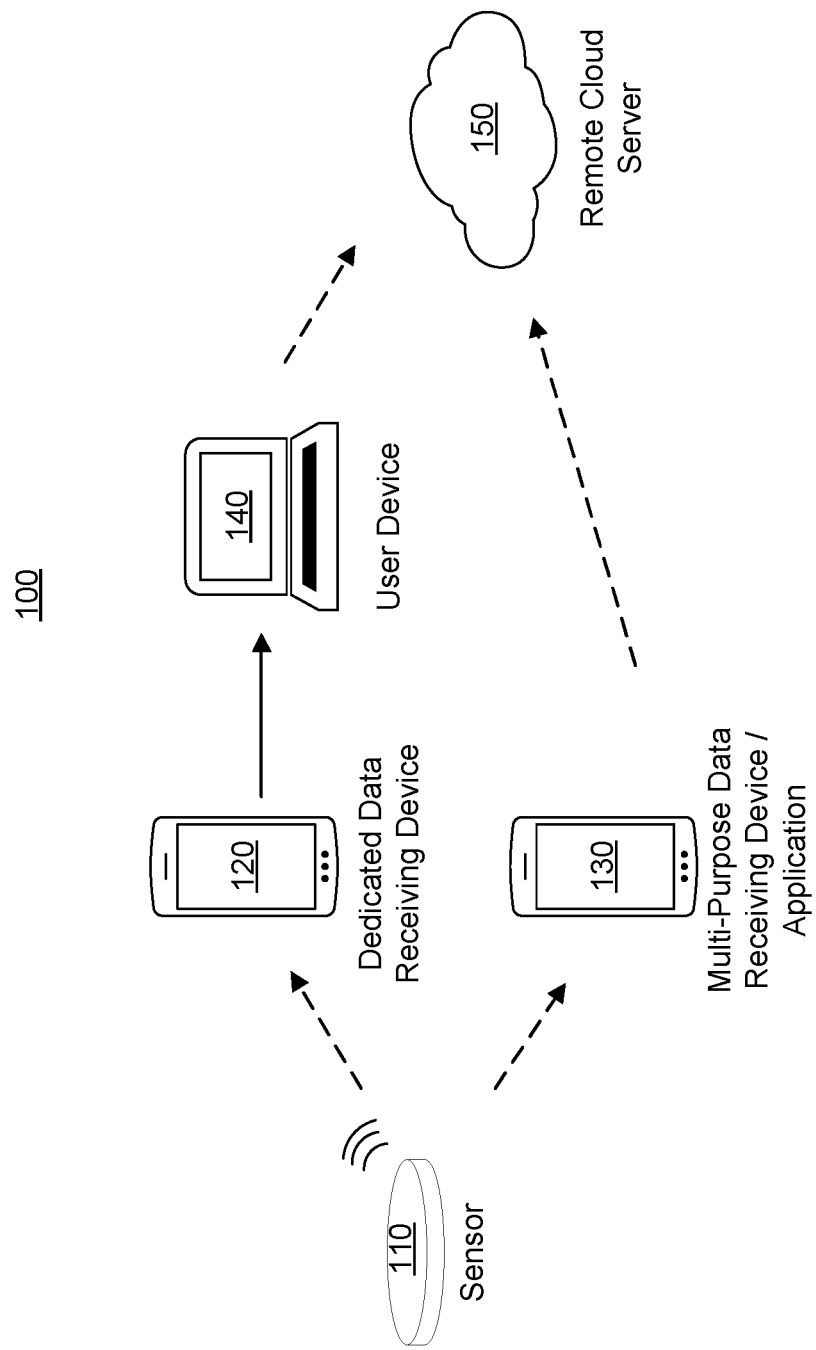
FIG. 1 is a diagram illustrating an operating environment of an example low-power medical monitoring system capable of embodying the techniques described herein.

Reference will now be made in detail to the various exemplary embodiments of the disclosed subject matter, exemplary embodiments of which are illustrated in the accompanying drawings. The structure and corresponding method of operation of the disclosed subject matter will be described in conjunction with the detailed description of the system The systems and methods presented herein can be used for secure communications in a medical monitoring system. For purpose of illustration of the disclosed subject matter, and not limitation, reference is made herein to secure communications using a medical device, such as a medical sensor. As used herein, "medical sensor" can refer to any device capable of receiving sensor information from a user useful for medical purposes, including for purpose of illustration but not limited to, body temperature sensors, blood pressure sensors, pulse or heart-rate sensors, glucose level sensors, analyte sensors, physical activity sensors, body movement sensors, or any other sensors useful for medical purposes. The purpose and advantages of the disclosed subject matter will be set forth and apparent from the description that follows. Additional advantages of the disclosed subject matter will be realized and attained by the methods, apparatus, and devices particularly pointed out in the written description and claims thereof, as well as from the appended drawings.

In one embodiment, a method for secured communication between a medical sensor and a computing device includes receiving, by the medical sensor, an authentication request from the computing device. The method includes generating, based on values provided in the authentication request, a challenge-response message for the computing device. The method includes receiving, from the computing device, a responsive challenge-response message. The method includes verifying that the responsive challenge-response message includes an expected value and corresponds to an expected format. The method includes, in response to verifying the responsive challenge-response message, sending a sensor secret value to the computing device. In accordance with the disclosed subject matter, for purpose of illustration and not limitation, methods for secured communication between a medical sensor and a computing device. Exemplary methods can include receiving by a medical sensor an activation signal from a computing device. The medical sensor can, in response to the activation signal, verify one or more authentication values associated with the computing device. In response to a successful verification, the medical sensor can begin to collect sensor information from a patient. As embodied herein, the sensor information can include medical data about the patient. As embodied herein, the medical sensor can receive the activation signal through a short-range communication protocol capable of delivering wireless power to one or more communication modules of the medical sensor. As embodied herein, the medical sensor can use information received through the short-range communication protocol to establish a connection with the computing device over a second short-range communication protocol without requiring additional verification from a user, including but not limited to the patient. As embodied herein, the short-range communication protocol can include Near-Field Communication (NFC) and the second short-range communication can include Bluetooth Low Energy (BLE). As embodied herein, the medical sensor can include less powerful computational resources than the computing device.

According to other aspects of the disclosed subject matter, systems and method can include receiving, by the medical sensor, an authentication request from a computing device. The medical sensor can use information included in the authentication request to generate a challenge response message for the computing device. As embodied herein, the challenge response message can be encrypted according to an agreed-upon encryption scheme. The medical sensor can receive a responsive challenge response message from the computing device and can further verify that the responsive challenge response message corresponds to an expected format and value. The medical sensor can subsequently send a sensor secret to the computing device. The sensor secret can also be encrypted according to an agreed-upon encryption scheme. As embodied herein, the sensor secret can include data unique to the medical sensor and random values. As embodied herein, the random value can be based on predefined values provided to the sensor, values generated by a communication module of the medical sensor, or values generated in response to user interactions. The medical sensor can encrypt one or more medical readings using an encryption key derived from the sensor secret and send the encrypted medical readings to the computing device. As embodied herein, the encryption key can be used with a specialized low-power stream cipher or block cipher. As embodied herein, the medical readings can include body temperature, heart rate, blood glucose levels, motion, and other medical readings.

According to other aspects of the disclosed subject matter, systems and methods can include receiving, by a first computing device from a medical sensor, a set of medical readings encrypted using a first key derived from a sensor secret and a first encryption algorithm. The sensor secret can include unique values associated with the medical sensor and random values generated by the medical sensor. The methods can include deriving, by the computing device, the first key based on the sensor secret. The methods can include decrypting, by the computing device, the set of medical readings using the derived first key. The methods can include encrypting the decrypted medical readings using a second key and a second encryption algorithm. The second key can include information unique to the computing device and random values generated by the computing device. The second encryption algorithm can be different, and as embodied herein, can be a more computationally complex encryption algorithm than the first encryption algorithm. The methods can include transmitting the encrypted medical readings to a second computing device. As embodied herein, the encrypted medical readings can be transmitted to second computing device via wired or wireless communication. The encrypted medical readings can be transmitted using a packet-level-encoding computing protocol. As embodied herein, the methods can include the second computing device decrypting the encrypted medical readings and transmitting them to a third computing device after encrypting the medical readings with the third key and a third encryption algorithm, where the first key, second key, and third key are all different and derived from different root values and where the first encryption algorithm, second encryption algorithm, and third encryption algorithm are all different. As embodied herein, the medical sensor can include less powerful computational resources than the first computing device. The first computing device can include less powerful computational resources than the second computing device.

For purpose of illustration and not limitation, reference is made to the exemplary embodiment of a medical monitoring system 100 for use with the disclosed subject matter as shown in FIG. 1. FIG. 1 illustrates an operating environment of a low-power medical monitoring system 100 capable of embodying the techniques described herein. The low-power medical monitoring system 100 can include a system of components designed to provide monitoring of medical statistics about a human or animal body or can provide for other medical operations based on the configurations of the various components. For example, the low-power medical monitoring system 100 can provide continuous glucose monitoring to users or can provide for the delivery of drugs and other medicants. As embodied herein, the system can include a low-power medical device 110, also referred to as a sensor worn by the user or attached to the body for which information is being collected. As embodied herein, the sensor 110 can be a sealed, disposable device, to improve ease of use and reduce risk of tampering, as discussed further herein. The low-power medical monitoring system 100 can further include a dedicated reading device 120 configured as described herein to facilitate retrieval and delivery of data, including medical data, from the sensor 110. As embodied herein, the low-power medical monitoring system 100 can, additionally or alternatively, include a software library or application licensed to a third-party and incorporated into a multi-purpose hardware device 130 such as a mobile phone, tablet, personal computing device, or other similar computing device capable of communicating with the sensor 110 over a communication link. Multi-purpose device 130 embodying and executing the software library can be said to form a data receiving device for communicating with the sensor 110. As used herein, a dedicated data receiving device 120 refers to a hardware device specifically manufactured for communicating with the sensor 110 within the low-power medical monitoring system 100 whereas a multi-purpose data receiving device 130 refers to a suitably configured hardware device which incorporates the software library or is executing the application. As used herein, a data communicating device refers equally to a dedicated data receiving device 120 or a multi-purpose data receiving device 130. It should be understood that the security architecture and design principles discussed herein are equally applicable to any suitably configured system involving a low-power medical device 110, a suitably configured dedicated data receiving device 120 or multi-purpose data receiving device 130, and other similar components as those described herein. The role of the low-power medical device 110 can be defined by the nature of the medical hardware embodied in the low-power medical device 110.

In general and at a high level, the low-power medical monitoring system 100 supports a minimal computation multi-factor (MCMF) scheme for generating authentication and encryption keys based on, among a variety of additional factors respective device identifiers, secret keys maintained by the devices and their manufacturer, and true random values. Using this technique, the various devices of the low-power medical monitoring system 100 spend minimal computing resources to perform authentication and computing functions. Moreover, the MCMF scheme does not necessitate any device of the low-power medical monitoring system be able to access a wide area network such as the Internet. Accordingly, the techniques of the present disclosure enable secure communications between low-power medical computing devices without substantially increasing the data processing load and power requirements. Additionally, because the disclosed security architecture and operations reduce the costs of computing components low-power medical monitoring system, the architecture can be suitable for use with a variety of medical devices (e.g., in place of the sensor 110), including ones that are mandated to be low-cost or disposable such as certain autoinjectors, on-body injectors, and sensors. Throughout this disclosure the low-power medical device 110 can be referred to as a sensor for simplicity.

As embodied herein, the sensor 110 can include small, individually-packaged disposable devices with a predetermined active use lifetime (e.g., 1 day, 14 days, 30 days, etc.). Sensors 110 can be applied to the skin of the patient body remain adhered over the duration of the sensor lifetime. As embodied herein, sensors 110 can be designed to be selectively removed and remain functional when reapplied.

Figure 2:
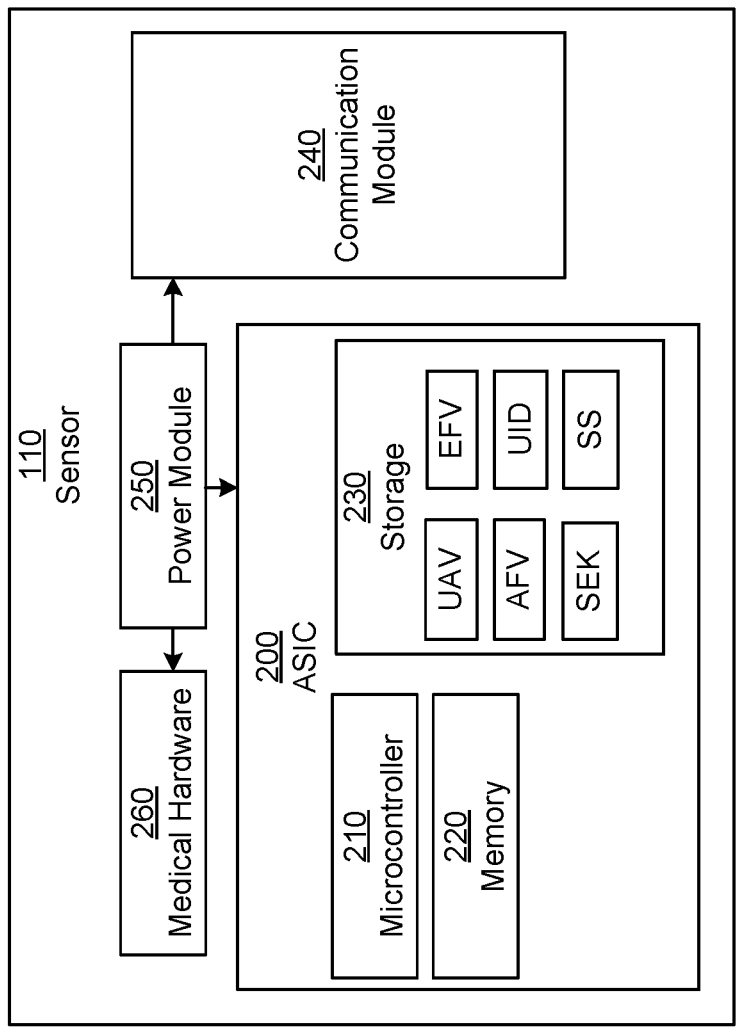
FIG. 2 is a block diagram illustrating an example sensor according to exemplary embodiments of the disclosed subject matter.

For purpose of illustration and not limitation, reference is made to the exemplary embodiment of a sensor 110 for use with the disclosed subject matter as shown in FIG. 2. FIG. 2 illustrates a block diagram of an example sensor 110 according to exemplary embodiments compatible with the security architecture and communication schemes described herein. As embodied herein, the sensor 110 can include an Application-Specific Integrated Circuit ("ASIC") 200 communicatively coupled with a communication module 240. As an example only and not by way of limitation, example communication modules 240 can include a Bluetooth Low-Energy ("BLE") chipset, Near-Field Communication ("NFC") chipset, or other chipsets for use with similar short-range communication schemes, such as a personal area network according to IEEE 802.15 protocols, IEEE 802.11 protocols, infrared communications according to the Infrared Data Association standards (IrDA), etc. The communication module 240 can transmit and receive data and commands via interaction with similarly-capable communication modules of a dedicated data receiving device 120 or multi-purpose data receiving device 130. As embodied herein, certain communication chipsets can be embedded in the ASIC 200 (e.g., an NFC antennae loop). As embodied herein, as the sensor 110 is designed to be power-efficient, low-cost, and possibly disposable, the ASIC 200 can include a microcontroller core 210, on-board memory 220, and storage memory 230. The storage memory 230 can store data used in the authentication and encryption security architecture disclosed herein. The data can have various elements and uses, including as described in the examples herein. The ASIC 200 can receive power from a power module 250, such as an on-board battery or from an NFC pulse. The power module 250 can store only a relatively small charge. As embodied herein, the sensor 110 can be a disposable device with a predetermined life span, and without wide-area network communication capability. As embodied herein, the communication module 240 can provide for communication under battery power. Although this disclosure is described with respect to exemplary configurations of the sensor 110 and the ASIC 200, other suitable configurations are envisioned. As an example, processing hardware of the sensor 110 can be implemented as another type of special-purpose processor, such as a field programmable gate array (FPGA). As embodied herein, the processing hardware of the sensor 110 can include a general-purpose processing unit (e.g., a CPU) or another programmable processor that is temporarily configured by software to execute the functions of the sensor 110. More generally, the processing hardware 30 can be implemented using hardware, firmware, software, or a suitable combination of hardware, firmware, and software. For purpose of illustration and not limitation, the processing hardware of the sensor 110 can be defined by one or more factors including computational capability, power capacity, memory capacity, availability of a network connection, etc.

To perform its medical functionalities, the sensor 100 can further include suitable medical hardware 260 appropriate to its function. As embodied herein, the medical hardware 260 can include, for example, an autoinjector prescribed to a patient for self-administering a drug or other medicament. Accordingly, the medical hardware 260 can include a mechanism that drives a needle or a plunger of a syringe in order to subcutaneously deliver a drug. The syringe can be pre-filled with the drug and can operate in response to a triggering event. For example, the mechanism can drive the needle into the patient and advance the plunger to deliver the drug subcutaneously via the needle.

As embodied herein, the low-power medical device 110 can be configured as an on-body injector attachable to a patient's body tissue (e.g., skin, organ, muscle, etc.) and capable of automatically delivering a subcutaneous injection of a fixed or patient-selected dose of a drug over a controlled or selected period of time. In such embodiments, the medical hardware 260 or low-power medical device can include, for example, an adhesive or other means for temporarily attaching the medical hardware 260 to the patient's body tissue, a primary container for storing a drug or medicament, a drive mechanism configured to drive or permit the release of a plunger to discharge the drug from the primary container, a trocar (e.g., a solid core needle), a flexible cannula disposed around the trocar, an insertion mechanism configured to insert the trocar and/or flexible cannula into the patient and optionally retract the trocar leaving the flexible cannula in the patient, a fluid pathway connector configured to establish fluid communication between the primary container and the flexible cannula upon device activation, and an actuator (e.g., a user displaceable button) configured to activate the device. As embodied herein, the on-body injector can be pre-filled and/or pre-loaded.

In addition to mechanical components, the medical hardware 260 can include electric and/or electronic components. For example, an electronic switch can be coupled to the mechanism. The low-power medical device 110 can establish an authenticated communication, receive an encrypted signal, decrypt the signal using the techniques of this disclosure, determine that the signal includes a command to operate the switch, and cause the switch to drive the needle. Thus, the low-power computing device embodied herein can be configured to perform a medical function using the medical hardware 260 in response to a remote command.

As embodied herein, the medical hardware 260 can include a travel sensor and an analog-to-digital converter to generate a digital signal indicative of the distance travelled by the needle or plunger. Upon delivering the medicament, the low-power medical device 110 can obtain a reading from the sensor, encrypt the reading using the techniques of this disclosure, and securely report the reading to the peer device 14. Additionally or alternatively, the low-power medical device 110 can report other measurements or parameters, such as a time at which the medicament was delivered, volume of medicament delivered, any issues encountered while delivering the medicament, etc. The low-power medical device 110 can be configured to provide data related to the operation of the medical hardware 260 to a remote device.

As embodied herein, the low-power medical device 110 can be configured to both receive encrypted data from a dedicated data receiving device 120 or multi-purpose data receiving device 130 and transmit encrypted data to the dedicated data receiving device 120 or multi-purpose data receiving device 130. The medical hardware 260 can be configured to implement any suitable combination of one or more medical functions and can include one or more sensing components. Such sensing components can be configured to detect an operational state of the low-power medical device 110 (e.g., unpackaged/ready for administration, sterile barrier removal, contact with patient's body tissue, cannula and/or needle insertion, drug delivery initiation, actuator or button displacement, drug delivery completion, plunger position, fluid pathway occlusion, etc.), a condition of the low-power medical device 110 or drug contained therein (e.g., temperature, shock or vibration exposure, light exposure, drug color, drug turbidity, drug viscosity, geographic location, spatial orientation, temporal information, ambient air pressure, etc.), and/or physiological information about the patient (e.g., body temperature, blood pressure, pulse or heart rate, glucose levels, physical activity or movement, fingerprint detection, etc.).

Referring still to FIG. 1, the ASIC 200 of the sensor 110 can be configured to dynamically generate authentication and encryption keys using the data retained within the storage memory 230. The ASIC 200 can be further configured to perform authentication procedures (e.g., handshake, mutual authentication, etc.) using received data and apply the generated key to sensitive data prior to sending the sensitive data to a dedicated data receiving device 120 or multi-purpose data receiving device 130 via the communication module 240. The generated key can be unique to the sensor 110, unique to a pair of devices (e.g., unique to a particular sensor-reader pair), unique to a communication session between a sensor 110 and dedicated data receiving device 120, unique to a message sent during a communication session, or unique to a block of data contained within a message. The techniques implemented by the ASIC 200 of the sensor 110 are discussed in more detail herein.

Figure 3:
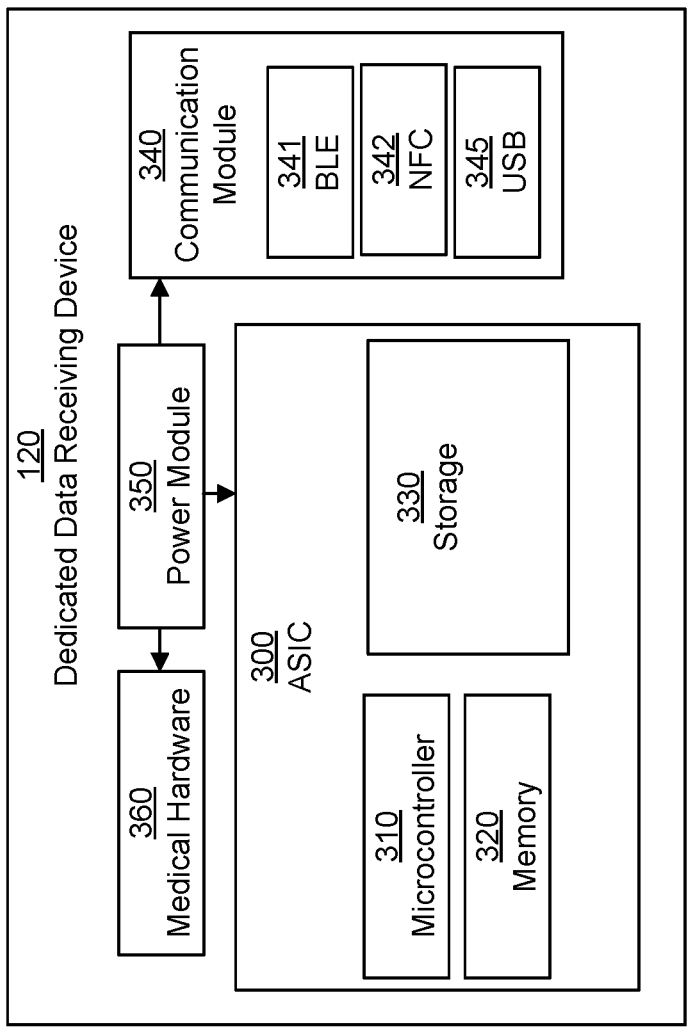
FIG. 3 is a block diagram illustrating an example dedicated data receiving device for communicating with the sensor according to exemplary embodiments of the disclosed subject matter.

For purpose of illustration and not limitation, reference is made to the exemplary embodiment of a dedicated data receiving device 120 for use with the disclosed subject matter as shown in FIG. 3. FIG. 3 illustrates an example dedicated data receiving device 120 compatible with the security and computing architecture described herein with respect to exemplary embodiments. As embodied herein, the dedicated data receiving device 120 can include a small-form factor device. The dedicated data receiving device 120 can optionally not be as memory- or processing-power constrained as the sensor 110, and as embodied herein, the dedicated data receiving device 120 can include sufficient memory for operational software storage and data storage, and sufficient RAM for software execution to communicate with sensor 110 as described herein. As illustrated in FIG. 3, the reader 130 includes an ASIC 300 including a microcontroller 310, memory 320, and storage 330 and communicatively coupled with a communication module 340. As embodied herein, the ASIC 300 can be identical to the ASIC 200 of the sensor 110. Alternatively, the ASIC 300 can be configured to include additional computing power and functionality. Power for the components of the dedicated data receiving device 120 can be delivered by a power module 350, which as embodied herein can include a rechargeable battery, allowing for sustained operations and continued use.

The dedicated data receiving device 120 can be configured to wirelessly couple with, or scan the sensor 110 and retrieve data, e.g., sensitive medical data, therefrom. As embodied herein, the dedicated data receiving device 120 can further include medical hardware 360 similar to, or expanded from, the medical hardware 260 of the sensor 110. As an example only, and not by way of limitation, in an embodiment in which the medical hardware 260 of the sensor 110 is configured for continuous glucose monitoring, the medical hardware 360 of the dedicated data receiving device 120 can be configured with a blood glucose meter, compatible for use with blood glucose test strips, thus expanding on the blood glucose monitoring of the sensor 110. As embodied herein, the dedicated data receiving device 120 can be configured to operate, with respect to the sensor 110 as described herein, as an NFC scanner and a BLE end point via specific modules (e.g., BLE module 341 or NFC module 342) of the communication module 340. As embodied herein, the dedicated data receiving device 120 can be configured for communication with via a Universal Serial Bus (USB) 345 of the communication module 340. As embodied herein, the on-board storage 330 of the dedicated data receiving device 120 can be capable of storing medical data received from the sensor 110 over an extended period of time. Further, the multi-purpose data receiving device 130 or a user computing device 140 as embodied herein can be configured to communicate with a remote cloud server 150 via a wide area network. As embodied herein, the sensor 110 can provide sensitive data to the dedicated data receiving device 120 or multi-purpose data receiving device 130. The dedicated data receiving device 120 can transmit the sensitive data to the user computing device 140. The user computing device 140 (or the multi-purpose data receiving device 130) can in turn transmit that data to a remote cloud server 150 for processing and analysis. In communicating with the cloud server 150, multi-purpose data receiving device 130 and user computing device 140 can generate unique user tokens according to authentication credentials entered by a user and stored at the respective device. The authentication credentials can be used to establish a secure connection to the remote cloud server 150 and can be further used to encrypt any sensitive data provided to the remove cloud server 150 as appropriate. As embodied herein multi-purpose data receiving device 130 and user computing device 140 can optionally not be as restricted in their use of processing power, and therefore, standard data encryption and transmission techniques can be used in transmitted to the remote cloud server 150.

Upon successful activation of the sensor 110 by a data receiving device (e.g., a dedicated data receiving device 120 or a multi-purpose data receiving device 130) the sensor 110 can be configured to collect medical data and makes that data available to the data receiving device. As an example, the data receiving device can pair with the sensor 110 over an NFC interface, providing short-range power to the sensor 110 and communicatively coupling with the sensor 110 over said NFC interface. As another example, the sensor 110 can pair with a data receiving device via corresponding communication modules and transmit medical data used for medical monitoring and alarms functions. Data from the dedicated data receiving device 120 can be uploaded to a user computing device ("PC") 140, for example over a USB interface 345 of the dedicated data receiving device 120. The user computing device 140 can further transmit data to a cloud server 150. USB connections can be authenticated on each plug event. Authentication can use a three-pass design with different keys, similar to the three-pass mutual authentication described herein with respect to FIG. 4. The USB system can support a variety of different sets of keys for encryption and authentication. Keys can be aligned with differential roles (clinical, manufacturer, user, etc.). Sensitive commands that could leak security information can trigger authenticated encryption using an authenticated additional keyset.

As used throughout this disclosure, Bluetooth Low Energy ("BLE") refers to a short-range communication protocol optimized to make paring of Bluetooth devices simple for end users. As described herein, the use of BLE on the sensor 110 can optionally not rely on standard BLE implementation of Bluetooth for security but can instead use application layer encryption using one or more block ciphers to establish mutual authentication and encryption. The use of a non-standard encryption design implemented in the application layer has several benefits. One benefit of this approach is that the user can complete the pairing of the sensor 110 and dedicated data receiving device 120 with only an NFC scan and without involving the user providing additional input, such as entering a security pin or confirming BLE pairing between the data receiving device and the sensor 110. Another benefit is that this approach mitigates the potential to allow devices that are not in the immediate proximity of the sensor 110 to inadvertently or intentionally pair, at least in part because the information used to support the pairing process is shared via a back-up short-range communication link (e.g., NFC) over a short range instead of over the longer-range BLE channel. Furthermore, as BLE pairing and bonding schemes are not involved, pairing of the sensor 110 can avoid implementation issues by chip vendors or vulnerabilities in the BLE specification.

As the data collected by the sensor 110 and exchanged between the sensor 110 and data receiving device pertain to medical information about a user, the data is highly sensitive and can be beneficial to be protected. Medical data associated with a patient is sensitive data at least in part because this information can be used for a variety of purposes, including for health monitoring and medication dosing decisions. In addition to patient data, the low-power medical monitoring system 100 can enforce security hardening against efforts by outside parties to reverse-engineering. The security architecture described herein can include various combinations of control features described herein, including, but not limited to: the protection of communication between devices; the protection of intellectual property within components and applications; and the protection of secrets and primary keying material. As embodied herein, encryption and authentication can be used as two of the primary technical controls for providing protective features. As embodied herein, the various components of the low-power medical monitoring system 100 can be configured compliant with a security interface designed to protect the Confidentiality, Integrity and Availability ("CIA") of this communication and associated data. To address these CIA concerns, the following security functions can be incorporated into the design of the hardware and software of the low-power medical monitoring system 100.

As embodied herein, to facilitate the confidentiality of data, communication connections between any two devices (e.g., a sensor 110 and dedicated data receiving device 120) can be mutually authenticated prior to transmitting sensitive data by either device. Communication connections can be encrypted using a device-unique or session-unique encryption key. As embodied herein, the encryption parameters can be configured to change with every data block of the communication.

As embodied herein, to guarantee the integrity of data, encrypted communications between any two devices (e.g., a sensor 110 and dedicated data receiving device 120) can be verified with transmission integrity checks built into the communications. As embodied herein, session key information, which can be used to encrypt the communication, can be exchanged between two devices after the devices have each been authenticated. Encrypted communications between a sensor 110 and a dedicated data receiving device 120 (or application executing on a multi-purpose data receiving device 130) can be validated with an error detection code or error correction code, including as an example and not by way of limitation, non-secure error-detecting codes, minimum distance coding, repetition codes, parity bits, checksums, cyclic redundancy checks, cryptographic hash functions, error correction codes, and other suitable methods for detecting the presence of an error in a digital message.

As embodied herein, minimum distance coding includes a random-error correcting code that provides a strict guarantee on number of detectable errors. Minimum distance coding involves choosing a codeword to represent a received value that minimizes the Hamming distance between the value and the representation. Minimum distance coding, or nearest neighbor coding, can be assisted using a standard array. Minimum distance coding is considered useful where the probability that an error occurs is independent of the position of a given symbol and errors can be considered independent events. These assumptions may be particularly applicable for transmissions over a binary symmetric channel.

Additionally or alternatively, as embodied herein, a repetition code relates to a coding scheme that repeats bits across a channel to guarantee that communication messages are received error-free. Given a stream of data to be transmitted, the data divided into blocks of bits. Each block is transmitted and re-transmitted some predetermined number of times. An error is detected if any transmission of the repeated block differs.

In addition, or as a further alternative, as embodied herein, a checksum is a value relative to a message based on a modular arithmetic sum of message code words of a fixed word length. The checksum can be directed from the entire message or a block of the message. Checksums are generated using a checksum function or cryptographic hash function that is configured to output significantly different checksum values (or hash values) for minor changes to the targeted message. A parity bit is a bit added to a group of bits in transmission to ensure that the counted number of certain bits in the outcome is even or odd. For example, the parity bit can be used to ensure that the number of bits with value 0 is odd. A parity bit can then detect single errors or a repeating fixed number of errors. A parity bit can be considered a special case of a checksum.

As embodied herein, to further reduce the risk of compromise of individual devices and the low-power medical monitoring system 100, root keys (e.g., keys used to generate device-unique or session-unique keys) can optionally not be stored on the sensor 110 and can be encrypted in storage on the dedicated data receiving device 120 (which can have additional processing power to decrypt the keys as needed). As embodied herein, the root keys can be stored in an obfuscated manner to prevent a third-party from easily accessing the root keys. The root keys can also be stored in different states of encryption based on where in the storage they are stored. As an example, the root keys can be stored in an unencrypted form in areas of the memory that are inaccessible to third-parties (e.g., because of other read- and write-locking mechanisms).

As embodied herein, to facilitate the availability of data, sensor 110 operations can be protected from tampering during service life, in which the sensor 110 can be designed as disposable, by restricting access to write functions to the memory 220 via a communication interface (e.g., BLE and NFC). Access to read functions of the memory 220 can also be enforced, especially where the read function attempts to access particular areas of the memory 220 that have been designated secure or sensitive. Additionally, the sensor 110 can be configured to only advertise and enter a connectable state when the sensor 110 becomes disconnected from a paired dedicated data receiving device 120. The sensor 110 can further shut down any communication connection request that does not complete authentication within a specified amount of time to safeguard against specific denial of service attacks on the communication interface. Furthermore, the general authentication and encryption design, described herein, can support interoperable usage where sensor 110 data can be made available to other "trusted" data receiving devices without being permanently bound to a single device.

As embodied herein, communication in the low-power medical monitoring system 100 involving sensitive data, for example medical data or security parameters described below, involves authentication. Commands related to such communication are re-authenticated for every operation as a three-way handshake implementing a challenge-response mechanism. For example and as embodied herein, a request for the challenge can be sent and a response containing challenge parameters is returned. The next request is in the form of an authentication token incorporating the first party challenge parameters and presenting the second party challenge parameters.

In the authentication scheme, mutual authentication between the sensor 110 and data receiving device can be protected by a device-unique encryption key that is stored in the sensor 110 and can be derived by the data receiving device from personalization values received by the data receiving device. Additionally, the mutual authentication can be protected by pre-shared device-unique keys between the sensor 110 and the data receiving device. Upon successful authentication, the sensor 110 can send a randomly-generated sensor-unique key. The sensor-unique key can be used as the base key for a stream cipher or block cipher. As embodied herein, inputs to the cipher can change with every encryption block.

Mutual authentication between the dedicated data receiving device 120 and a user computing device 140 can occur over wired or other wireless communication. The communication can be mutually authenticated between the dedicated data receiving device 120 and a proprietary application executing on the user computing device 140. Encryption keys for authentication and for the communication exchange can be derived from root keys incorporated into the dedicated data receiving device 120 and application encryption library.

The message payload between the sensor 110 and data receiving device can be encrypted with a device-unique key. The device-unique key can render any attempts at meaningful tampering or interception of the message contents difficult as compromise of a single device-unique key can allow a malicious party to decrypt message payloads from that device but cannot be used to decrypt message payloads from other devices. As embodied herein, the implementation of the encryption can use counter mode of a block cipher as a stream cipher for efficiency. In such a mode, a single-bit flip within a message leads to single-bit message corruption. Such corruption using counter mode and stream ciphers can be mitigated by verification of message transmission integrity with an error detection code of an appropriate length.

Figure 4:
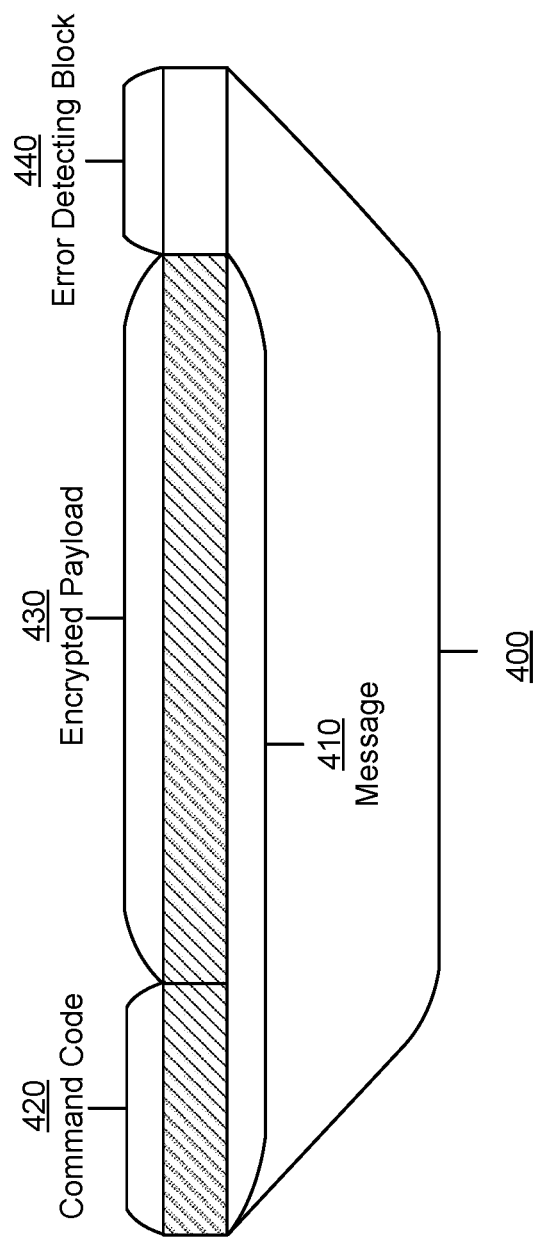
FIG. 4 is a diagram illustrating an example structure of a message payload according to exemplary embodiments of the disclosed subject matter.

For purpose of illustration and not limitation, reference is made to the exemplary embodiment of a structure of a message payload for use with the disclosed subject matter as shown in FIG. 4. FIG. 4 illustrates an example structure of a message payload according to exemplary embodiments. In the example shown in FIG. 4, the error detection code is computed over the entire message 410 including the plaintext command code 420 and encrypted payload 430. The error detecting block 440, appended to the communication block 400, can be used to ensure the integrity of the message 410.

Sensor operation can be protected from tampering during use service life via the communication module 240 by two complementary approaches. First, the ability to write to the memory 220 (including software) of the sensor 110 via a communication interface (e.g., NFC) can be disabled at time of manufacture. Ports on the ASIC for debugging and reprogramming can be selectively de-activated based on an activate security state of the sensor 110. Additionally or alternatively, and as embodied herein, the sensor 110 can be configured without the ability to support write functions via other communication interfaces (e.g., BLE).

As embodied herein, the sensor 110, dedicated data receiving device 120, and multi-purpose data receiving device 130 can each employ a variety of security practices to ensure the confidentiality of data exchanged over communication sessions and facilitate the relevant devices to find and establish connections with trusted endpoints. As an example, the sensor 110 can be configured to advertise and enter a connectable state, for example over a BLE interface, when it becomes disconnected from a paired dedicated data receiving device 120. The sensor 110 can only enter the connectable state for a predetermined amount of time in every fixed period of time, for example, for two seconds in every two-minute period. The sensor 110 can further deny and shut down connection requests if the requestor cannot complete a proprietary login procedure over a communication interface within a predetermined period of time (e.g., within four seconds). These characteristics safeguard against specific denial of service attacks, and in particular against denial of service attacks on a BLE interface. As embodied herein, the identifiers used to connect to the sensor 110 can be mutable to reduce the ability to track a single sensor 110 as it connects to one or more data receiving devices. Connection identifiers for the sensor 110 or data receiving device can include, as an example only, a unique or semi-unique device identifier, a media access control address for the communication module of the device, a device address configured for the particular communication protocol (e.g., a BLUETOOTH address, etc.), internet protocol address, an identifier assigned to the device by the low-power medical monitoring system, a universally-agreed identifier for the type of device that is broadcasting, etc. The sensor 110 can change identifiers between sensor 110 activation and pairing with the first dedicated data receiving device 120. If the sensor 110 disconnects from the first dedicated data receiving device 120 during its active use timeline, the sensor 110 can change the connection identifier on disconnection or on receiving a request for a new connection with a second dedicated data receiving device 120.

Additionally or alternatively, the connection identifier can be changed according to the connection type or based on cryptographic features of communication protocol and supported by the multi-purpose data receiving device 130 or dedicated data receiving device 120. As embodied herein, the representation of the connection identifier can be modified using one or more cryptographic functions before the connection identifier is broadcast by the device (e.g., by the sensor 110 or a data receiving device). The device can operate in a privacy mode where several functions are performed simultaneously to mask and secure the connection identifier to reduce the risk that the connection identifier will be uniquely associated to the broadcasting device. One such function can include randomizing aspects of the connection identifier prior to broadcast. The connection identifier can also be encrypted with an agreed cryptographic function and public key. Then, only devices that have the corresponding private key or a shared secret key, know the type of cryptographic function used, and can deterministically undo the randomization effects will be able to identify the specific device. As embodied herein, these levels of cryptographic security can be performed at an application layer or at a higher infrastructural layer in the communication protocol.

As embodied herein, the sensor can support establishing long-term connection pairs by storing encryption and authentication keys associated with data receiving devices, or support a data receiving device storing an encryption and authentication key for the sensor 110 for a prolonged period of time. For example, the sensor 110 or data receiving device can associate a connection identifier for the other party to the exchange in association with the encryption and authentication keys used by the other party. In so doing, the sensor 110 can establish connections with a data receiving device more quickly, at least in part because sensor 110 can avoid establishing a new authentication pairing with that data receiving device and can proceed directly to exchanging information via the encrypted communication protocols described herein. After a connection is successfully established, the two devices can refrain from broadcasting connection identifiers and other information to establish a new connection and can communicate using an agreed channel-hopping scheme to reduce the opportunity for third-parties to listen to the communication. As another example, the sensor 110 can be configured to scan available connection points and prefer connections with those devices to which it has already connected, such as those devices which the sensor 110 has previously established an authenticated exchange. This process can reduce the opportunity for malicious third-parties to intersect an authentication exchange when other trusted data receiving devices are within communication range.

Additionally or alternatively, the sensor 110 and data receiving devices can support the use of whitelists for known trusted devices. For example, a user that envisions using multiple sensors 110 over the use lifetime of a data receiving device can register connection identifiers associated with multiple sensors or can register a range of connection identifiers. Similarly a sensor 110 can be configured with a trusted connection identifier or range of connection identifiers (e.g., secured values associated with a dedicated data receiving device 120 or multi-purpose data receiving device 130 belonging to a particular user). As such, when establishing a connection, the sensor 110 and data receiving device can compare connection identifiers associated with available connection points with the connection identifiers stored in the whitelist. The whitelist can represent an exclusive range, meaning that no connection identifiers besides those included in the whitelist will be used. Alternatively, the whitelist can represent a preferred range, in which the whitelist is searched first, but other devices can still be used. As embodied herein, the sensor 110 and data receiving device can be configured to confirm the identity of a device that was accepted via any of the shortcut procedures described above and can disconnect and reject future connections with devices that are suspected of providing fraudulent identifiers and authentication address.

Certain commands compatible with the sensor 110 can be referred to based at least in part on a level of security used prior to performing the commands. For example, certain commands can be referred to as "open" or "non-authenticated" commands. Such commands can include commands that result in no changes to the sensor 110 or retrieval of sensitive medical information, for example the retrieval of a battery status indication of the sensor 110 or the retrieval of information to initiate authentication. Other commands can be referred to as "authenticated" commands. Such commands can include commands that result in the collection of sensitive data. As embodied herein, the communication path between a sensor 110 and data receiving device can be re-authenticated for every authenticated command. As embodied herein, the low-power medical monitoring system 100 can be designed as a so-called "fail open" system so that a user with multiple data receiving devices can utilize any of the data receiving devices instead of establishing an exclusive binding. For example, an exclusive binding would preclude a user from activating and authenticating with a first data receiving device for instance, and subsequently using an unpaired second data receiving device from receiving medical data. Such a use case is desirable to support third-party multi-purpose data receiving devices 130.

Figure 5:
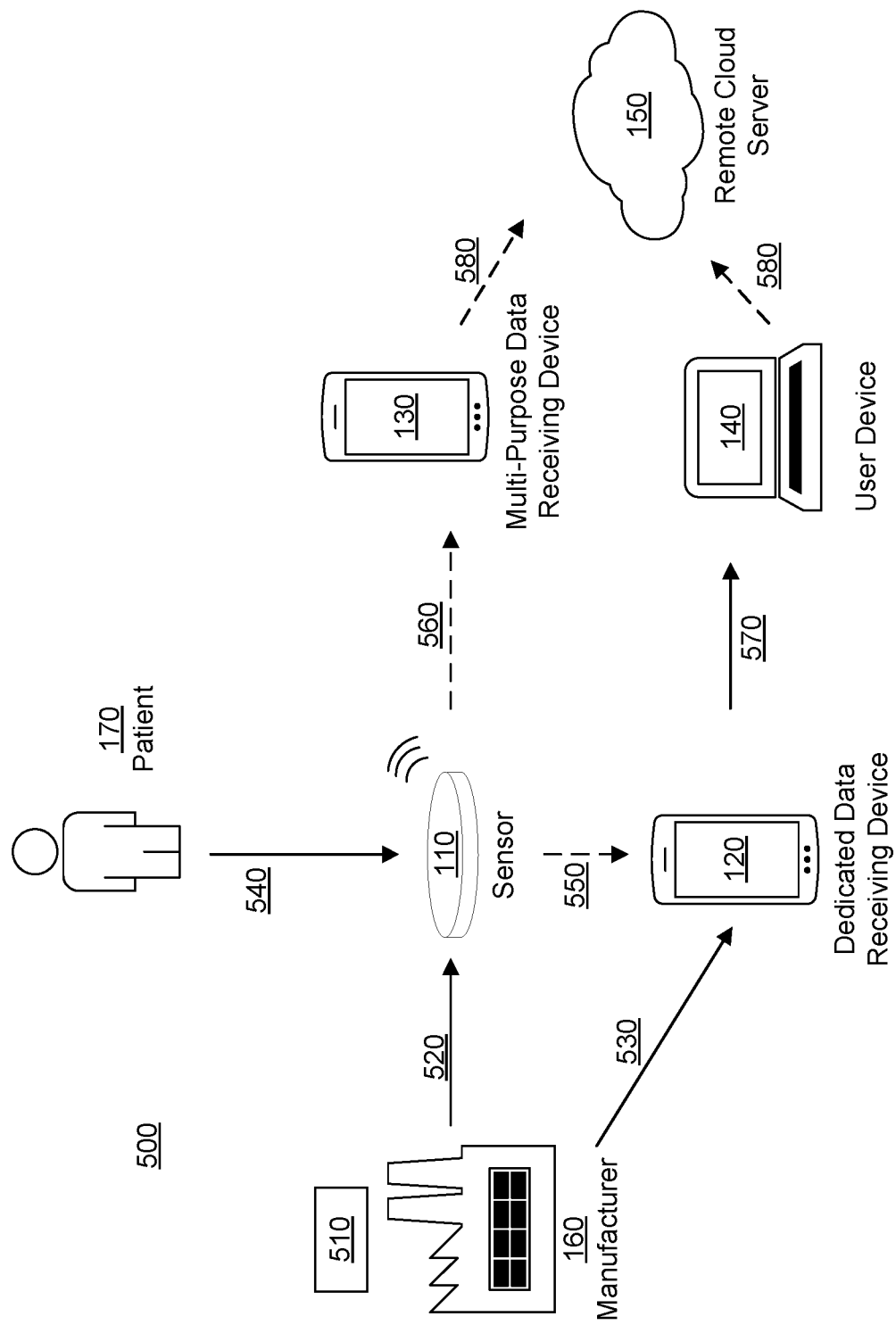
FIG. 5 is a diagram illustrating an example operational flow and data lifecycle of the low-power medical monitoring system.

The high-level security architecture of the low-power medical monitoring system 100 will now be described with reference to FIG. 5. FIG. 5 illustrates an exemplary embodiment of an operational flow and data lifecycle 500 of the low-power medical monitoring system 100 for use with the disclosed subject matter. At step 510, the manufacturer 160 chooses information that can be used to generate encryption keys for each device. As embodied herein, the information can include secured root keys for the sensor 110 and optionally for the dedicated data receiving device 120 that can be used in combination with device-specific information and operational data (e.g., entropy-based random values) to generate encryption values unique to the device, session, or data transmission as need. At step 520, the manufacturer can imbue each sensor 110 with a unique identifier ("UID"). The manufacturer can further imbue each sensor 110 with other identifying information, such as an identifier for the manufacturer, identifier for the communication module and manufacturer, or any other suitable identifying information for the sensor or sensor components. For example, the UID for each sensor 110 can be derived from sensor-unique data, such as from a serial number assigned to each ASIC 200 embodied in the sensor 110 by the ASIC vendor, from a serial number assigned to a communication module 240 embodied in the sensor 110 by a communication module vendor, from a random value generated by the sensor manufacturer, etc. Additionally or alternatively, the UID can also be derived from manufacturing values including a lot number for the sensor 110 or its components, a day, date, or time of manufacturer of the sensor 110 or its key components, the manufacturing location, process, or line of the sensor or its key components, and other information that can be used to identify when and how the sensor was manufactured. The UID can be accompanied by encryption keys and several generated random values that are also unique to each sensor 110. At step 530, the manufacturer can provide each dedicated data receiving device 120 with data including root keys that can be used, for example, to derive data encryption keys for the purposes of facilitating communication.

At step 540, the sensor 110 can collect medical data, such as from a patient or user 140 (e.g., a human or animal body). For example, the sensor 110 can collect data at predetermined intervals upon activation by a properly configured dedicated data receiving device 120. At step 550, the sensor 110 can transmit the medical data to a dedicated data receiving device 120 over a communication interface via its communication module 240 (e.g., via NFC, BLE, etc.). In addition to the medical data, the sensor 110 can transmit additional information to facilitate exchange along the chosen protocol. For example, message payloads from the sensor 110 to the dedicated data receiving device 120 can include manufacturer-specific values, manufacturer-identifying values, identifying values for the sensor, transmission power level values, etc. As embodied herein, power level values can be defined on a range established by the chosen communication interface (e.g., on a range of 0 to 20). The power level value can be used by the dedicated data receiving device 120 to request the sensor 110 to rebroadcast data or to perform future data transmissions at a high power level. For example, a sensor 110 can be at a distance from the dedicated data receiving device 120 that makes ensuring communication integrity difficult. The dedicated data receiving device 120 can send instructions to the sensor 110 to cause the sensor 110 to divert more power to the communication model 240 of the sensor 110 to ensure that transmissions are delivered intact.

At step 560, the sensor 110 can optionally transmit the medical data to a multi-purpose data receiving device 130 over a communication interface via its communication module 240 (e.g., via NFC, BLE, etc.). At step 570, the dedicated data receiving device 120 can be communicatively coupled to a proprietary application executing on a user computing device 140 (e.g., a personal computer of the patient). Through communication with the proprietary application, the dedicated data receiving device 120 can communicate medical data retrieved from the sensor 110. As embodied herein, the dedicated data receiving device 120 can be provided to end users in a firmware-locked state, with the internal program flash of the ASIC 200 of the dedicated data receiving device 120 shipped with debug and programming ports locked, preventing access without a mass erase. As embodied herein, the sensor 110 or dedicated data receiving device 120 can be returned to the manufacturer 160 (or a trusted third-party) for diagnostic purposes, such as recovery of inaccessible data or to determine the cause of certain errors.

At step 580, the multi-purpose data receiving device 130 or user computing device 140 can, as embodied herein, communicate medical data to a cloud server 150. As described herein, the multi-purpose data receiving device 130 or user computing device 140 can optionally not be as restricted in their use of computer processing power and can therefore engage in standard data security approaches in transmitting the data to the cloud server 150. The communication exchanges between the multi-purpose data receiving device 130 or user computing device 140 and the cloud server 150 can involve exchanges and confirmation of the data transmitted. As an example, the cloud server 150 can generate additional information from the data provided to the cloud server 150 and can provide that additional information to the user computing device 140 or multi-purpose data receiving device 130 so that a user of the device (e.g., the patient 140) can view the additional information. As embodied herein, prior to the data being uploaded to the cloud server 150, personally identifying information for the patient 140 can be removed from the data, encrypted, or otherwise obscured to anonymize the data prior to upload. The cloud server 150 can associate that data back with the patient 140 (if needed) using other information, e.g., the authentication token used to connect to the cloud server 150 or identifying information for the multi-purpose data receiving device 130 or associated with the user computing device 140. Alternatively, the data can be irreversibly de-associated with the patient 140 to ensure privacy of the data is maintained while still allowing for data to be used for researching, for example to monitor or improve the accuracy of the techniques used to process the data. Furthermore, the data can be compared against previously received data to ensure that the data is not a duplicate of another data set. For example, a patient 140 can use both a multi-purpose data receiving device 130 and a user computing device 140 to upload data, which should not be double-counted for the patient 140.

The data lifecycle described with respect to FIG. 5 illustrates areas where sensitive data, for example security parameters (described in further detail herein) or patient data can risk being exposed to, or be open to potential attack from, malicious third-parties. For example, encryption keys are embedded for use in the manufacturing process and security parameters are delivered to the sensors 110 and readers 120. Medical data exchanged between a sensor 110 and a multi-purpose data receiving device 130, a sensor 110 and a dedicated data receiving device 120, or a dedicated data receiving device 120 and proprietary application executing on a user computing device 140, over a communication link (e.g., NFC, BLE, USB, etc.) are exchanged remote from the control of the manufacturer 160, and thus communication must be secured through, e.g., authenticated and encrypted. Sensor 110 and dedicated data receiving device 120 logs, e.g., those retrieved from the relevant device upon return to the manufacturer 160 have minimal medically-sensitive data, however re-enabling manufacturer-specific interfaces to retrieve said logs can expose security parameters and manufacturer-specific commands. Thus, as embodied herein, manufacturer-specific interfaces are authenticated via separate manufacturer-specific processes (e.g., using a manufacturer-specific device-unique or session-unique key).

The security architecture described herein embodies several design principles to guide the security-related decisions. As an example, parameters that can be used with authentication or encryption and are transmitted as plain-text are transformed prior to use as security parameters. As part of the device identification and authentication sequences, sensor properties such as UID, software version, randomly generated challenges, and nonce values can be transmitted as plain-text and thus risk being directly observable. As embodied herein, these parameters are processed in some way, such as through a non-cryptographic transform or algebraic manipulation prior to use as inputs to cryptographic or other security functions.

Communication transmission integrity is actively managed using on-chip hardware functions. While encryption provides a secure means of transmitting data in a tamper-proof manner, encryption and decryption are computationally expensive processes. Furthermore, transmission failures cannot be differentiated from attacks. As described previously, a fast, hardware-based error detection code can be used for transmission integrity. As an example, as embodied herein, an appropriately-sized error detection code for the length of the message (e.g., a 16-bit CRC) can be used, although this disclosure anticipates other suitable hardware-based error detection codes. Functions involving additional security rely on encryption.

Challenge parameter order varies between sender 110 and data receiving device (e.g., to sensor 110 from data receiving device and vice versa) to decrease likelihood of success of a replay attack. An abstract risk of using parameters that coincidentally align with cipher block boundaries can create a situation where coincident values paired with a challenge produce the same ciphertext. Authenticated exchanges vary (e.g., reverse, transform, etc.) the order of challenge parameters in return tokens to reduce this risk to the rare case where random challenge A is equal to random challenge B AND the coincident parameters have equivalent value, a 1-in-264 probability. Challenges can be used for single exchanges and nonces can be used for single messages. To further reduce the risk of ciphertext collisions, challenges used in mutual authentication tokens can be discarded and regenerated for every new authenticated exchange and nonce values can be changed for every message. To address the risks associated with a known-plaintext attack, values used as inputs to counter mode ciphers begin with non-zero values to reduce predictability.

A sensor 110 can receive exemplary Security Parameters ("SPs") and keys during manufacture. A sensor 110 can be provided a static, Unique ID ("UID") that can, as embodied herein, include an Organizationally Unique Identifier ("OUI"), manufacturer identifying code, or other similar information. The UIDs can be tracked and verified to be unique. The UID can be non-mutable hardware-coded value. During manufacturer, sensors 110 can further receive Personalization Values ("PVs") and encryption keys, including, but not limited to an Authentication Formation Value (AFV), an Encryption Formation Value (EFV), or a Unique Authentication Value (UAV), described in further detail herein. As embodied herein, Personalization Values can be used as starting material for nonces, which in turn can be used as inputs to ciphers used during authentication and data encryption, while Formation Values can include random values used to further obfuscate a relationship between a Personalization Value, other key information, and the output. Personalization values can also include keys such as an Identity Resolving Key ("IRK") that can be used by the sensor 110 or a data receiving device to de-anonymize connection identifying information (including, but not limited to the information described herein) and resolve anonymized or signed connection identification information to refer to a particular device for the purposes of identifying and initiating an authentication exchange. The AFV and EFV can be random values generated by a manufacturer 160 and stored in the sensor 110. The AFV can be used as input to various ciphers used during authentication, while the EFV can be used during encryption. As embodied herein, the AFV and EFV can be differing or matching values. The UAV can be a value derived from unique information of the sensor 110, for example, from the various components of the sensor, such as the ASIC 200 and communication module 240.

As embodied herein, the sensor 110 can be configured to independently derive or expand keys. Thus, the sensor 110 can receive encryption keys in the form of an expanded key schedule. Because at time of manufacture, all inputs to generating key values (e.g., root keys, device-unique information, secret sensor values, etc.) are known, keys can be expanded prior to the provisioning of the sensor 110. For example, the sensor 110 can receive a random secret used to implement sensor-unique keys prior to transmitting the sensitive data to a data receiving device at the conclusion of, or as part of a concluding step to, an authentication sequence with the data receiving device. The sensor 110 outside the supervision of the manufacturer 160 can be subject to potential attacks, and thus certain key values are not stored on the sensor 110. For example, keys used to derive communication authentication values, or sensor-unique authentication values can optionally not be permanently stored on the sensor 110 but are instead determined live and as needed from the values stored on the sensor 110. Moreover, sensor-unique keys that are used to authenticate restricted commands can also be stored elsewhere than the sensor 110 or can be stored in a format that reduces the impact of compromise. As embodied herein, an unrelated sensor-unique keying secret (e.g., "SS") is randomly generated during sensor 110 manufacture based on device-unique values, manufacturing-associated values, random-value functions, and other conditioning functions. The values used to generate SS are used to create uniqueness of the secret. Random-value functions obscure the relationship between the SS, root keys, and derivative keys. This secret can be used during operation to communicate with a data receiving device after combination with a root key available to the data receiving device. The root key can be stored by the data receiving device to derive a Sensor Encryption Key ("SEK") that is unique to that sensor 110 and used to encrypt data communications between the sensor 110 and data receiving device.

SPs are inputs to the controls in the security architecture. For example, SPs are used as input to the encryption functions and affect the output of ciphers. To clarify, the cipher is applied to the data; in particular, data is not used as a SP. Example SPs that can be used in a low-power medical monitoring system 100 are described herein. Derivative values of the SPs are not recited for brevity but should be understood to be employed where appropriate.

The system architecture contemplates the use of a variety of stored and generated security keys during security-critical processes, such as device authentication, encryption for inter-device communication, software and firmware updating, etc. As described previously, because the sensor 110 of the low-power medical monitoring system 100 is designed with power- and computing—efficiency in mind, the sensor 110 can store certain values that correlate with the security keys. To enable authentication and encryption, the values (such as SPs) can be used by a data receiving device to generate appropriate session- or device-unique security keys. As embodied herein, the key structure can be utilized to resist cryptographic compromise by preferring derived keys for authentication and encryption and using each derived key for a single purpose or activity. As embodied herein, derived keys can be unique to each device (e.g., sensor 110, dedicated data receiving device 120, multi-purpose data receiving device 130) and can be further configured to be unique to each purpose (e.g., a particular communication session between two devices, or even a particular exchange during the communication session). Thus, compromise of a single derived key (such as a key used for authentication or encryption) is isolated to a compromise of a single function of a single sensor 110. Compromise of a single key does not introduce significant weakness to the overall cryptographic system.

In generating authentication keys, encryption keys, and root keys generally (which can be used for key derivation of single device-specific encryption keys or single-purpose ephemeral encryption keys) security practices are followed to ensure that the keys are generated in a secure, tamper-proof, and, where needed, truly random manner. In practice, keys can be generated in part using system entropy collected through, for example, true random behavior, such as minute user interaction (e.g., mouse movement), system interrupts, network interrupts, process table events, and other system entropy collection techniques.

Example keys, including without limitation example usage of and relationships among keys, in the security architecture for the low-power medical monitoring system 100 as embodied herein are described herein. The keys used and described herein are exemplary and not exclusive, and additional or alternative keys can be used as appropriate based on the design requirements and use for the particular medical monitoring system 100. For example, and as embodied herein, where SEK is described as being used to encrypt communications between a sensor 110 and a multi-purpose data receiving device 130, a similar key can be used to encrypt communication between a dedicated data receiving device 120 and a user computing device 140.

While SEK can be unique, the impact of a non-unique SEK can be considered minimal in the overall security architecture due at least in part to authentication redundancy. For example, if two users have sensors 110 with the same values of SEK (which for n-bit keys represent an odds of $1:2^n$), matching values of the data nonce used for the cipher (which for n-byte nonce, represent an odds of $1:2^n$), and matching values of a communication interface binding identifier, the sensors 110 can still be configured to only communicate with the activating data receiving device that is actively bonded at the hardware handshake level if hardware addresses match.

As embodied herein, true randomness can be incorporated throughout the security architecture. Randomness can be derived by different entities in the system, including the manufacturer 160, the sensors 110, dedicated data receiving devices 120, multi-purpose data receiving devices 130, and user computing device 140. A Random Bit Generator ("RBG") creates completely unpredictable (e.g., true random) output. The unpredictable output is used to drive generation of keys or other cryptographic parameters and ensure that an outside party cannot algorithmically predict bits before they are made available.

As embodied herein, entropy provided by a manufacturer 160 is provided to the sensors 110 through a combination of proprietary software and open and auditable software. Random values provided to the sensors 110 are used for various purposes, including, but not limited to, authentication nonce input for communication links and random material used as input to a Key Derivation Function. In the security architecture, UAV and AFV can be used as initial values for nonce construction and, by virtue of their random nature, make output more unpredictable. Furthermore, as embodied herein, once the sensor 110 has been activated by a user, the nonce values gain additional entropy from user interaction and the significance of the manufacturing values is overtaken by the entropy of the user interaction. For example, entropy can be introduced through unpredictable variables such as time of interaction, time period between interactions with a dedicated data receiving device 120 or multi-purpose data receiving device 130, through the communication module 240 etc. For example, where the sensor 110 includes a communication chipset supporting true random values, the sensor 110 can gather entropy from the chipset. As embodied herein, calls to generate random values from the microcontroller 210 of the sensor 110 can be fulfilled through a chipset vendor-provided programming interface ("API").

Like the sensor 110, the dedicated data receiving device 120 can use true random values and can gather entropy via its various sensors. As an example, the dedicated data receiving device 120 can include a communication chipset 340, separate from the communication chipset 240 of the sensor 110, that supports a true random capability. As embodied herein, the dedicated data receiving device 120 can implement an RBG architecture where entropy from the True Random capability is used as a live entropy source and conditioned by a PRNG using a random entropy source (or values derived therefrom) as input. The software library and application within the dedicated data receiving device 120 can retrieve random data from the True Random capability and store those values in non-volatile memory as a seed to the available cipher as a PRNG. Furthermore, third-party applications incorporating the software library can provide additional entropy function through the target platform embedded operating environment.

As embodied herein, the low-power medical monitoring system 100 can employ periodic key rotation to further reduce the likelihood of key compromise and exploitation. The key rotation strategy employed by the low-power medical monitoring system 100 can be designed to ensure backward compatibility of field-deployed or distributed devices. As an example, the low-power medical monitoring system 100 can employ keys for downstream devices (e.g., devices that are in the field or cannot be feasibly provided updates) that are designed to be compatible with multiple generations of keys used by upstream devices. Upstream devices can be defined relative to their downstream, reliant devices and based on the ease with which the device can be updated with new keys under the security architecture. As an example, a user computing device 140 executing a proprietary application can be considered upstream of a multi-purpose data receiving device 130 or dedicated data receiving device 120, which is in turn considered upstream of a sensor 110. As another example, rotation of root keys can begin with the manufacturer 160. During manufacture of a new key generation of sensors 110, the manufacturer 160 can propagate the new generation of keys to newly manufactured sensors 110. The manufacturer 160 can also push updates to data receiving devices that enable the data receiving devices to identify a security version returned by a sensor 110 to determine which root key to use when deriving the authentication key for a particular sensor 110. As a further alternative, key rotation can be based on an agreed-upon schedule, where the devices are configured to adjust the keys used according to some time- or event-driven function. After the occurrence of the triggering event, all authenticate devices are configured to switch to another generation of keys, pre-programmed for the devices. The triggering event can be universal to all relevant devices (e.g., switching keys on a monthly, daily, or weekly basis), can be unique to the individual device (e.g., switch a key for a sensor after 24 hours of active use), or can be applied to any subdivision of the devices.

As embodied herein, the encryption scheme described herein can involve several functions related to, for example, cryptographic performance. One class of these functions include symmetric encryption functions so that the same key can be used to encrypt outbound data and decrypt inbound data. Included in this class of functions can be block ciphers or related families of functions. A block cipher refers to an encryption function that applies a deterministic algorithm with a known key to encrypt a block of values, rather than encrypting one bit at a time as in stream ciphers. A block cipher can be particularly useful in the system architecture of the low-power medical monitoring system 100 because, as described previously, the sensor 110 (and to a lesser extent, the dedicated data receiving device 120) can have less available computing power due at least in part to design options selected to control cost, reduce size and preserve battery life. However, stream cipher algorithms can be used according to the techniques disclosed herein with appropriate modifications to account for power and computing resources restrictions of this system architecture. Encryption algorithms that can be used include any suitable cipher techniques.

As an example, the low-power medical monitoring system 100 can support a first, lightweight block cipher or stream cipher for cryptography. As another example, the low-power medical monitoring system 100 can further support additional, more cryptographically complex, block ciphers or stream ciphers for cryptography. In particular embodiments, the first, lightweight block cipher or stream cipher can be preferentially used for devices having less access to power and computing potential, while a second block cipher or stream cipher can be a more cryptographically complex block cipher or stream cipher for use by devices with fewer restrictions on power and computing resources. The first block cipher or stream cipher can be chosen for implementations where the volume of data produced and transmitted is relatively small, rendering the more complex cryptography of the second block cipher or stream cipher unsuitable or impractical. The first block cipher or stream cipher can therefore be referred to as a lightweight block cipher or lightweight stream cipher in comparison to the second block cipher or stream cipher. The low-power medical monitoring system 100 can support the use of additional block ciphers and stream ciphers as appropriate. Each of the block ciphers and stream ciphers can be performed by software modules or dedicated hardware modules.

As an example, a lightweight block cipher can employ an add-rotate-xor ("ARX") framework. In this example, no schedule key is used. Given the data to be encrypted and key, each split into at least four blocks, the algorithm begins xoring each block of the data with the corresponding block of the key. The algorithm proceeds through a predetermined number of rounds of a permutation function, with the number of rounds being chosen to balance security and performance. Each round of the permutation function can include the following the operations performed in order: add the second block of data to the first block of data; rotate the second block a predetermined amount; xor the first block to data to the second block of data; rotate the first block of data a predetermined amount; add the fourth block of data to the third block of data; rotate the third block of data a predetermined amount; xor the third block of data to the fourth block of data; add the fourth block of data to the first block of data; rotate the fourth block of data a predetermined amount; xor the first block of data to the fourth block of data; add the second block of data to the third block of data; rotate the second block of data a predetermined amount; xor the third block of data to the second block of data; and rotate the third block of data a predetermined amount. As a final step, after the predetermined number of rounds, the algorithm again xors each block of the data in the current state with the corresponding block of the key.

As another example, a lightweight block cipher can employ an ARX algorithm. Given the block to be used with the cipher split into two words and a key, the algorithm can progress for a predetermined number of rounds. During each round, the bits of the first word of the block are rotated by a first predetermined amount, the second word of the block is added to the first word of the block, the key is xored into the first word of the block, the bits of the second word of the block are rotated by a second predetermined amount, and the first word of the block is xored into the second word of the block. As embodied herein, the keys used for each round can be computed on-demand or pre-cached depending on available computing resources.

As another example, a lightweight stream cipher can make use of xor, 32-bit addition, and constant-distance rotation. The cipher can be represented by an internal state including sixteen words arranged as a square matrix. The words include four predetermined words, eight words of key, two words of stream position, and two words of nonce. The cipher operates by performing four quarter-round operations per round, with rounds alternating by operations on the rows or columns of the internal slate. The quarter-round operations performed per round receive as input four words and perform a set series of xor, addition, and rotation operations on the input words. In a first example, the quarter-round operations follow the pattern: the addition of the first and four words are rotated by a predetermined amount and xored with the second word; the addition of the first word and second word is rotated by a predetermined amount and xored with the third word; the addition of the second word and third word is rotated by a predetermined amount and xored with the fourth word; and the addition of the third word and the fourth word is rotated by a predetermined amount and xored with the first word. The predetermined amounts can vary for each operation. After a set number of rounds, the mixed array is added to the original internal slate to prevent recovery of the initial key. A variant of the stream cipher can involve a rearranged internal slate and variations on the quarter-round operations. The quarter operations can be modified to still receive four input words, with the quarter-round operations following the pattern: the second word is added to the first word; the resulting first word is xored with the fourth word; the result is rotated by a predetermined amount; the new fourth word is added to the third word; the resulting third word is xored with the second word; the result is rotated by a predetermined amount. This pattern is repeated with different values for the predetermined-rotation. Each quarter-round updates each word twice. Additionally, the stream cipher can be modified so that quarter-rounds operated on the columns and diagonals instead of the columns and rows.

As an example, a more cryptographically complex block cipher can employ a predetermined number of rounds consisting of expansion, key mixing, substitution and permutation. Prior to the main set of rounds, the block can be divided into two halves, which each half being alternately processed to facilitate symmetry in encryption and decryption. During expansion, the current half-block is expanded by duplicating half of the bits in the half-block so that the block includes a set of operative bits comprising a copy of four input bits and copy of immediately adjacent bit from each side of the input bits. During the mixing step, a subkey is combined with the expanded half-block using xor the exclusive-or operation. The subkeys are determined according to a key schedule based on the main encryption key. After the subkey has been mixed the block is divided into a number of substitution boxes. Each substitution box reduces the count of its input bits according a non-linear transformation provided by a lookup table. The bits output from the substitution step are rearranged according to a predetermined permutation. The operations to form the key schedule can involve retrieving a subset of the bits of the key, dividing the subset, performing a bitwise rotation by a predetermined amount and recombining the two halves to form the subkey.

As another example, a more cryptographically complex block cipher can be based on a substitution-permutation network. The cipher can include operations such as a key expansion step, in which round keys are derived from a cipher master key using a predefined key schedule, and an initial key addition step in which each byte of the block is xored with a byte of the round key. The operations can include a predetermined number of rounds in which one or more of the following steps occur: each byte is replaced with another byte in a non-linear substitution step according to a lookup table; selected bytes are shifted cyclically for a certain number of steps with the shift amount varying incrementally; subdivisions of the bytes are mixed through an invertible linear transformation; and the round key is xored into the resulting block.

As another example, a more cryptographically complex stream cipher can generate a pseudorandom stream of bits, or keystream, which is combined with the data to be encrypted using xor. The keystream is generated using a key-scheduling algorithm. In the key-scheduling algorithm, an internal array is initialized to the identity permutation of a predetermined length. For a set number of rounds equal to the predetermined length, an internal value is derived by adding the current value of the internal value, the value stored at the position of the internal array corresponding to the round number, and the value of the position of the key determined by performing the modulo of the round number to the length of the key. The internal value is then set to the modulo of the result of this operation and the maximum number of rounds. To end the round, values of the internal array at the positions indexed by the round number and the internal value are swapped. Once the key-scheduling algorithm has been completed, a pseudo-random generation algorithm modifies the state of the internal array and outputs a byte of the keystream. Encrypted data is achieved by xoring the output byte of the keystream with a byte of the data to be encrypted. In each iteration of the pseudo-random generation algorithm, a first internal value is incremented. A second internal value is assigned the value of the second internal value incremented by the value of the internal array at the position of the first internal value. The values of the internal array at the positions indexed by the first internal value and the second internal are swapped. The value of the keystream is then output as the value of the internal array at the position indexed by the addition of the values of the internal array at the first internal value and second internal value. To prevent index out of bounds errors, where values are used to index the internal array, a modulo can be performed between the value and the length of the internal array.

Moreover, block cipher or stream cipher implementations can be chosen based on known weaknesses or attack vectors. As an example, known attacks against a cipher can be evaluated and compared against the volume of data that will be generated, including during the entire active use life of a sensor 110, as a method of evaluating worst case scenarios regarding malicious third-parties. As described above, several of the keys are derived from device-unique values, and as such, including a single key or cipher reduces the potential impact. Additionally, the amount of compromised values needed to conduct a supply-chain level attack, e.g., to learn the value of root keys, significantly restricts the practicality of such attacks. As described herein, sensors 110 use a randomly generated key for SEK, and key recovery attempts against SEK have little long-term value.

As embodied herein, the particular implementation of a cipher, e.g., the selection of block size and key size can be made based on the size of data blocks to be transmitted over the various communication interfaces supported by the communication module (e.g., communication module 240 and communication module 340). For example, as embodied herein, data blocks transmitted over NFC or BLE can be aligned on 8-byte boundaries, and a 64-bit cipher block size can be chosen. As embodied herein, the particular implementation of the cipher can be made based on desired encryption strength, leading to a change in the selection cipher block size. A stronger cipher typically involves more computational overhead and imposes additional time to decrypt data, e.g., during mutual authentication exchanges. Additionally, the cipher block size can be chosen based on the computing architecture of the microcontroller 210 of the ASIC 200 of the sensor 110 and the communication protocol used between the sensor 110 and data receiving devices. As embodied herein, the key size made be selected based on the particular memory constraints of the computing platforms used.

As embodied herein, sensors 110 can use a separate Sensor Authentication Key ("SAK") for authentication. As described, SAK is used to protect authentication exchanges, which are composed of security challenges. The SAK is a sensor-unique key derived from a root key available to data receiving devices and sensor-unique security parameters. The root key can be stored by the dedicated data receiving device 120 or multi-purpose data receiving device 130 and used during sensor authentication. Each SAK can be derived by the data receiving device for each authentication exchange. The SPs are subject during communication to transformation prior to use by the Key Derivation Function to derive each SAK. Without knowledge of the ciphertext output (SAK) or how the SPs are transformed and used by the Key Derivation Function, an attacker lacks the plaintext input and is unable to attack root keys, ensuring its security under this security architecture. During encryption exchanges, the initial encrypted block contains a sender-generated random value followed by a transformed security challenge. Without access to both random values and the non-cryptographic transform, an attacker is not given the opportunity to harvest plain-text input to attack SAK, ensuring its security under this security architecture.

As embodied herein, the sensor 110 can be configured to respond to requests from a data receiving device with either plain-text or encrypted responses. Responses eliciting plain-text response include commands that do not involve authentication. As an example only and not by way of limitation, a non-authenticated command can include a sensor information retrieval (SIR) command to which a sensor 110 returns the sensor UID and a software version. Encrypted responses are protected by, for example, the sensor-unique derived key SAK or the sensor-unique random key SEK. Authentication exchanges can be protected by SAK while data communications over communication links such as memory block reads can be protected with SEK.

An authenticated command can involve the command request to follow a specified format, where the values for the format are synchronized from a prior exchange. This procedure can be used to reduce the impact of randomized probing attempts from third parties. The authenticated command format can be retained as proprietary information available only to a manufacturer 160 or service provider. Prior to issuing an authenticated command request, the data receiving device and sensor 110 can first synchronize values for the exchange challenges (e.g., a sender challenge response (SCR) and receiver challenge response (RCR)) and to synchronize the initial nonce. Synchronization can be accomplished by completing a security challenge message exchange.

As embodied herein, the challenge random values (e.g., SCR and RCR) can be sourced from a true random value generator function provided by, for example, a communication module of the sensor 110 or data receiving device. The security challenges can be exchanged as unique payloads and can be saved in persistent memory for later use as an authentication parameter when sending or verifying authenticated commands. The nonce can be derived from the AFV and other internal state variables stored on the sensor 110.

In addition to validating these security exchange values, additional security functions can be performed to harden the low-power medical monitoring system 100 against attacks such as replay attacks and signal leakage. As an example, prior to executing an authenticated command, the sensor 110 can be configured to verify that the values of SCR and RCR are valid for the current exchange. Once an authenticated command has been successfully completed, to prevent replay attacks the sensor 110 can increase an authenticated command counter and set the state of SCR and RCR to invalid in the current exchange context. As another example, if a data receiving device sends an improper authentication token after a security challenge response, the sensor 110 can be configured not to provide a valid response to avoid signal leakage.

Figure 6:
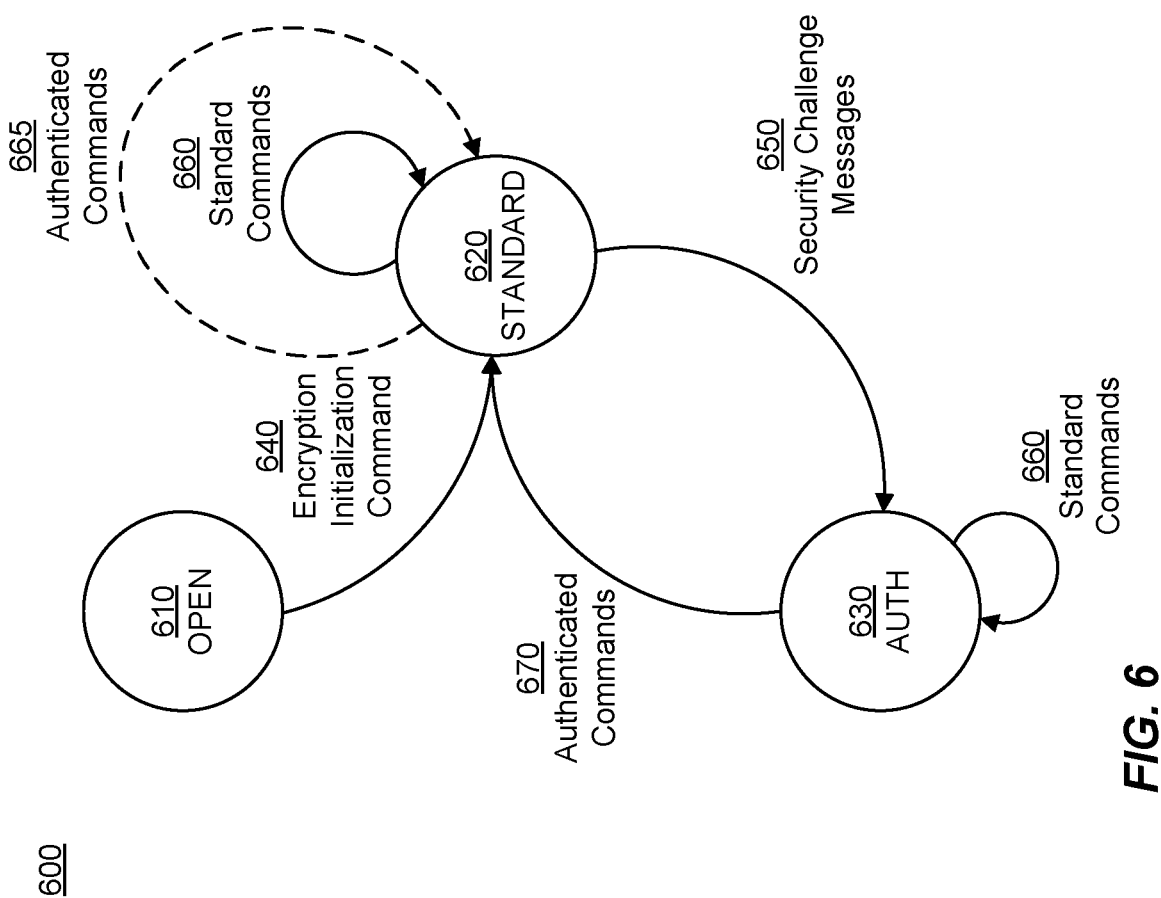
FIG. 6 is a diagram illustrating an example of a messaging response state machine according to the disclosed subject matter.

For purpose of illustration and not limitation, reference is made to the exemplary embodiment of a messaging response state machine 600 of the sensor 110 for use with the disclosed subject matter as shown in FIG. 6. FIG. 6 illustrates a messaging response state machine 600 of the sensor 110. The state machine 600 reflects three states, an openly programmable state in which the sensor 110 can be programmed (OPEN 610) and two regular states (STANDARD 620, AUTH 630). As embodied herein, in the state OPEN 610, the sensor 110 is be capable of being programmed, reprogrammed, and personalized. For example, ports on the ASIC 200 of the sensor 110 for debugging and reprogramming can be enabled. Prior to the sensor 110 being provided for remote/non-manufacturer use, the sensor 110 can be transitioned to the first regular state STANDARD 620 when it receives an encryption initialization command 640.

In the first of the two regular states STANDARD 620, the sensor 110 can be configured to respond to all supported standard messages 660 and security challenge messages 650. Upon receiving a valid command, the sensor 110 transitions back to STANDARD 620 as shown. If a sensor 110 receives an authenticated command 665 in this state, the sensor 110 can respond with deterministic values or not respond at all. If the sensor 110 receives a security challenge message 650, the sensor 110 can service the request and upon successful negotiation of the authentication, as described above, can transition to the state denoted AUTH 630.

As embodied herein, the AUTH state 630 can be characterized by the sensor 110 receiving and responding to all standard commands 660 available in the STANDARD state 620 in addition to receiving and responding to requests for authenticated commands 670. If the sensor 110 receives a properly authenticated command, the sensor can service the command and transition back to the STANDARD state 620.

One example authenticated command can be a mutual authentication command. As embodied herein, mutual authentication functions at communication module-interface boundaries can verify the integrity of a data path across components. As embodied herein, mutual authentication can be based on mechanisms for authentication of two entities to each other with no on-line trusted third party to verify establishment of a secret key via challenge-response.

As an example, and not by way of limitation, mutual authentication functions can implement a two-pass authentication in which the sensor 110 and data receiving device are authenticated. The sensor 110 can initiate the sequence by sending an authentication request or by generating and sending a first token to the data receiving device. The first token can be encrypted according to a previously-established cryptographic scheme (e.g., a pre-shared key and cryptographic function). The first token can include a time-variant value or sequential value, an identifier corresponding to the sending party, an identifying constant value, and a text field. On receipt of the first token, the data receiving device verifies the token by decrypting any encrypted portion and checks all included values for accuracy and expected values. The data receiving device then generates and second a second token to the sensor 110. The second token can also be encrypted according to the previously-established cryptographic scheme. The second token can include a sequentially-next time-variant value or sequential value, an identifier corresponding to the sensor 110, an identifier corresponding to the data receiving device, an identifying constant value, and a text field. On receipt of the second token, the sensor 110 verifies the token by decrypting any encrypted portion and checks all included values for accuracy and expected values by comparing any returned values to the expected sent values. The order of the values included in the token can vary in the tokens to cause messages to appear unrelated regardless of the cipher algorithm chosen.

Figure 7A:
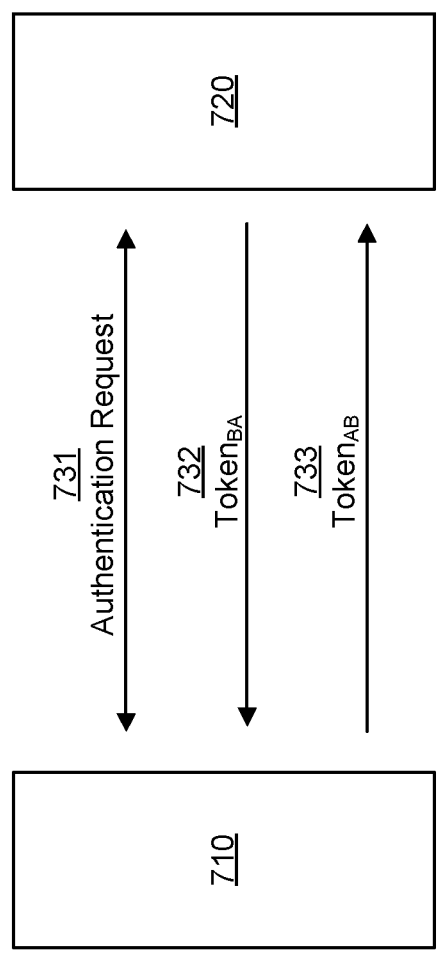
FIGS. 7A-7D are diagrams illustrating examples of mutual authentication schemes according to the disclosed subject matter.

For purpose of illustration and not limitation, reference is made to the exemplary embodiment of a mutual authentication scheme for use with the disclosed subject matter as shown in FIG. 7A. The two-pass mutual authentication scheme will be described with respect to FIG. 7A. In the mutual authentication scheme, an authentication request 731 can optionally be exchanged between the requesting party 720 (e.g., a sensor 110) and a receiving party 710 (e.g., a data receiving device). The requesting party 720 can generate and send a first token $Token_{BA}$ at step 732. As described herein, $Token_{BA}$ can include a time-variant value or sequential value, an identifier corresponding to the requesting party 720, an identifying constant value, and a text field. The time-variant value can, for example, include a timestamp associated with generating the token or associated with initiating the authentication request. The sequential value can be, for example, a nonce generated using an agreed-upon nonce function. The time-variant value and sequential value can be used to confirm that a token is not being reused at some point by an unauthorized entity. The identifier corresponding to the requesting party 720 can also be used to ensure that an authorized party is not attempting to masquerade as the requesting party 720. After receiving the token, the receiving party 710 can decrypt the $\text{Token}_{BA}$ according to an expected key and verify the contents of the token, e.g., verify that the time-variant value is accurate and that the identifiers correspond to the proper entity. The expected key can, for example, be a key derived from pre-shared secret values or be a key established based on identifying information for the two parties. Upon verification of the expected values, the receiving party 710 generate a send a second token $\text{Token}_{AB}$. As described herein, $\text{Token}_{AB}$ can be similar to $\text{Token}_{BA}$ and include an advance time-variant value, the next value based on the sequential value, the identifier corresponding to the requesting party 720, an identifier corresponding to the receiving party 710, an identifying constant value, and a text field. These values serve similar functions for the benefit of the requesting party 720. As an example, the inclusion of the identifying values for both the requesting party 720 and receiving party 710 can permit the requesting party 720 to validate its decryption process while validating the exchange. The receiving party 710 can encrypt the $\text{Token}_{AB}$ and, at step 733 send the token to the requesting party 733. The requesting party 733 can then decrypt the token using the agreed-upon cryptographic scheme and validate the information contained therein. Through this mutual authentication process, the requesting party 720 and receiving party 710 can validate that the encryption scheme is mutually acceptable and that the parties to the communication are as expected.

As another example, and not by way of limitation, mutual authentication functions can implement a three-pass authentication based on checking random values in a challenge-response sequence. In the challenge-response sequence, the data receiving device can initiate the sequence by sending a request for challenge parameters to the sensor 110. The sensor 110 can respond with the requested parameters. The data receiving device can then present a first authentication token to the sensor 110. The sensor 110 can respond with a second authentication token. As embodied herein, the lengths of variables included in the security challenge messages, for example, SCR and RCR, can be variable and can be chosen to align or not align with an encryption block boundary in order to reduce the predictability of discovery. Additionally, the order of the parameters SCR and RCR in the security challenge messages can vary in the authentication token to cause messages to appear unrelated regardless of the cipher algorithm chosen.

Figure 7B:
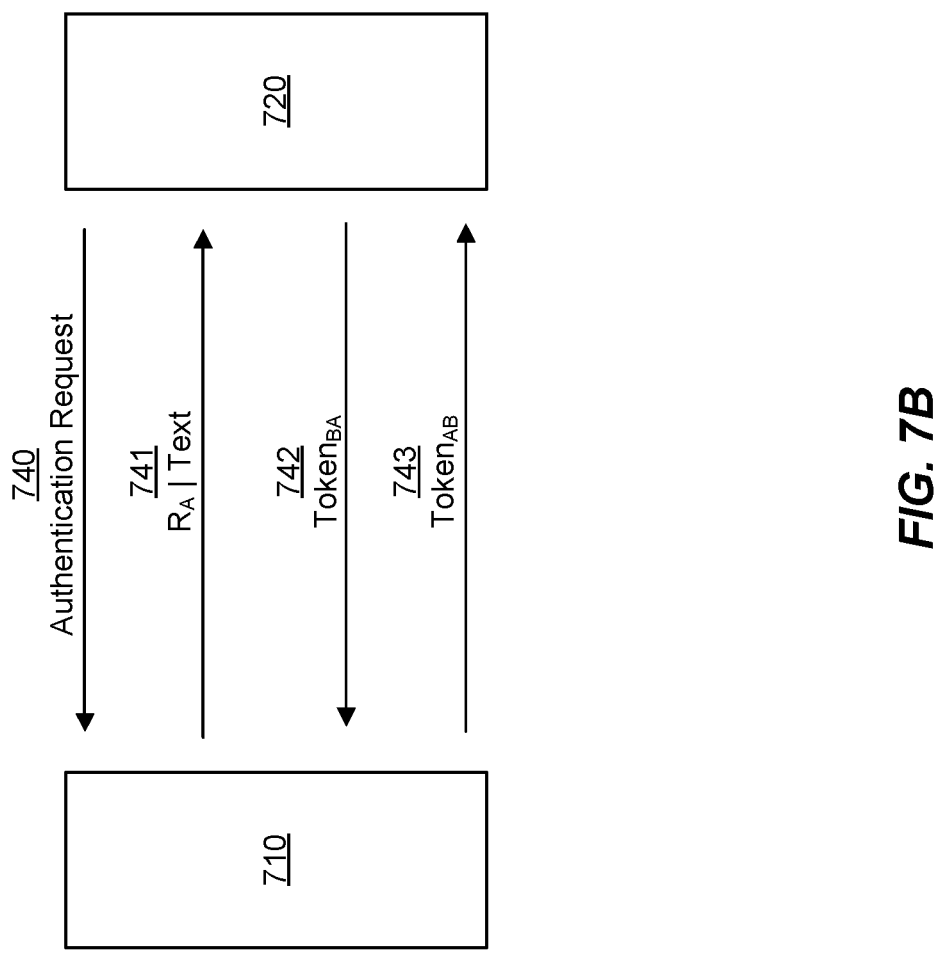

For purpose of illustration and not limitation, reference is made to the exemplary embodiment of a mutual authentication scheme for use with the disclosed subject matter as shown in FIG. 7B. The three-pass mutual authentication scheme will be described with respect to FIG. 7B. In the three-pass mutual authentication scheme, once an authentication request 740 is initiated by a requesting party 720 (e.g., a sensor 110), the receiving party 710 (e.g., a data receiving device) returns plain-text challenge parameters 741 ($R_A$ concatenated with Text) as shown in FIG. 7B. The requesting party 720 can originate additional challenge parameters and embed those parameters along with a representation of the challenge into an encrypted token 742 ($\text{Token}_{BA}$). The receiving party 710 can verify the contents of the token 742 and return a separate token 743 ($\text{Token}_{AB}$) incorporating at least a representation of the challenge parameters provided by the requestor 720 with token contents re-ordered to address possible replay of ciphertext. As embodied herein, the encrypted token $\text{Token}_{AB}$ 743 can include command specific data between challenge parameters. With this exchange of parameters, the data receiving device encrypts the challenge parameter SCR and demonstrates to the sensor 110 several pieces of information, which permit the sensor 110 to validate that the data receiving device can be authenticated. This information includes that the data receiving device can successfully derive SAK from the pre-shared secret, root keys, and sensor-specific parameters such as UAV. This information also includes that the data receiving device can successfully implement the secret message protocol by incorporating challenge parameter SCR into a message with RCR. The information can also include that the data receiving device can encrypt with the derived key SAK and apply the synchronized nonce value.

Upon receipt and verification of the authentication token $\text{Token}_{BA}$, the receiving party 710 (e.g., sensor 110) returns the parameter RCR. In doing so, the sensor 110 demonstrates several pieces of information to the sending party 720 (e.g., data receiving device), from which the data receiving device can validate that the sensor 110 can be authenticated. This information includes that the sensor 110 has knowledge of SAK. This information includes that the sensor 110 can decrypt the authentication token to recover RCR using SAK and the synchronized nonce. The information also includes that the sensor 110 can implement the message protocol and return RCR in a new message protected by SAK with an appropriately derived subsequent nonce to the provided synchronized nonce derived from the progression of values from a predefined function.

As another example, and not by way of limitation, mutual authentication functions can implement a four-pass authentication in which the sensor 110 and data receiving device are authenticated by use of a trusted third party. During the four-pass authentication, the data receiving device can start authentication by generating and sending a first token to the trusted third party. Additionally, or alternatively, the authentication can begin with the sensor 110 sending an authentication request to the data receiving device, which triggers the data receiving device to generate and send the token to the trusted third party. The first token can include a time-variant value, an identifier corresponding to the data receiving device, and a text field. On receipt of the first token, the trusted third party generates a random key for use by the data receiving device and the sensor 110 and generates and sends a responsive token to the data receiving device. The responsive token includes two portions. A first portion includes a first identifying constant, a time-variant parameter or random value (used to differentiate the first portion from the second portion), the time-variant parameter received from the data receiving device, the random key, an identifier for the sensor 110 and text. The second portion includes a second identifying constant, another time-variant parameter or random value, the random key, an identifier for the data receiving device and text. Each portion of the responsive token can be encrypted according to a previously-established cryptographic scheme (e.g., a pre-shared key and cryptographic function) between two parties. The first portion can be encrypted using a key shared between the data receiving device and the trusted third party. The second portion can be encrypted using a key shared between the trusted third party and the sensor 110.

On receipt of the responsive token, the data receiving device decrypts any encrypted portion using the key shared between the data receiving device and the trusted third party and confirms the expected time-variant parameter or random value of the first portion. The data receiving device checks the correctness of the identifier for the sensor 110 and confirms the time-variant parameter sent to the trusted third party. The data receiving device then retrieves the random key from the decrypted portion of the responsive token and extracts the second portion of the token and uses it to construct a token to be sent to the sensor 110. The token for the sensor 110 includes the extracted second portion and an additional portion including another time-variant value, an identifier for the data receiving device, and text. The data receiving device then sends the token to the sensor 110. On receipt, the sensor 110 checks the correctness of the identifier for the data receiving device and the value of the time-variant value. The sensor decrypts the second portion, which includes the random key provided by the trusted third party. The sensor 110 then encrypts and sends a message for the data receiving device using the random key provided by the trusted third party. The message contains a final sequentially-next value of the time-variant parameter. On receipt, the data receiving device confirms that the values of the message are correct after decrypting the message using the random key from the trusted third party. As before, the order of the values included in the token can vary in the tokens to cause messages to appear unrelated regardless of the cipher algorithm chosen.

Figure 7C:
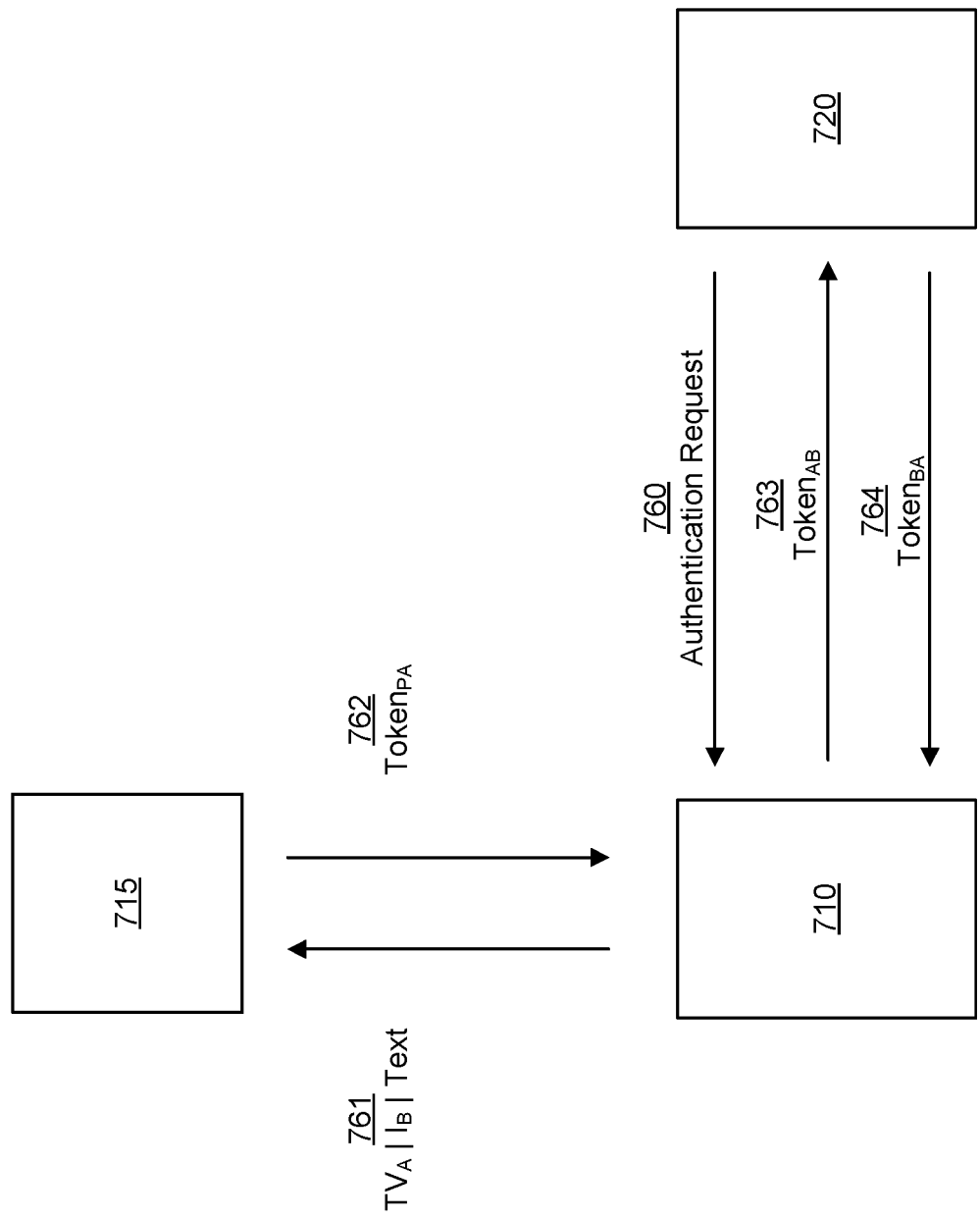

For purpose of illustration and not limitation, reference is made to the exemplary embodiment of a mutual authentication scheme for use with the disclosed subject matter as shown in FIG. 7C. The four-pass mutual authentication scheme will be described with respect to FIG. 7C. In the four-pass mutual authentication scheme, once an authentication request 760 is initiated by a requesting party 720 (e.g., a sensor 110), the receiving party 710 (e.g., a data receiving device) sends a request to the trusted third party 715 (e.g., a remote cloud server 150 associated with the low-power medical monitoring system 100) at step 761. The request includes at least a time-variant, non-repeatable value ($TV_A$), an identifier for the requesting party 720 ($I_B$) and text. $TV_A$ can optionally be a random value. The request need not be encrypted at this time. At step 762, the trusted third party generates and sends a responsive token $Token_{P4}$. $Token_{P4}$ is used to share a random key for use for communication between the requesting party 720 and the receiving party 710. $Token_{P4}$ is characterized by including two portions which are each encrypted using a separate key. A first encrypted portion is encrypted using a key shared between the trusted third-party 715 and the receiving party 710. The second encrypted portion is encrypted using a key shared between the trusted third party 715 and the requesting party 720 (e.g., the sensor 110). The first portion includes the random key, the time-variant non-repeatable value sent by the receiving party 710, an identifier for the requesting party 720, and text. The second portion includes another time-variant value, the random key, and an identifier for the receiving party 710. The trusted third party sends this token to the receiving party 710 at step 762.

The receiving party 710 decrypts the first portion of the $Token_{P4}$ and verifies its contents. The receiving party 710 can confirm that the time-variant value matches that sent by the receiving party 710 to ensure that the message is not a repeat of a previous response to a key-request message. The receiving party 710 can also confirm that the identity of the requesting party 720 is correct. The receiving party 710 can then construct a $Token_{AB}$ to be sent to the requesting party 720. The $Token_{AB}$ includes the encrypted second portion of the $Token_{P4}$ (still encrypted because the receiving party 710 does not have access to the key shared between the trusted third party and the requesting party 720), and another portion encrypted using the random key provided by the trusted third party. This other portion includes at least a time-variant value that will be used to confirm accuracy of the requesting party's decryption. At step 763, the receiving party 710 sends this $Token_{AB}$ to the requesting party 720. The requesting party 720 receives the token and first decrypts the portion encrypted using the key shared between the trusted third party 715 and the requesting party 720. The requesting party 720 verifies the information in the encrypted portion, by, for example, confirming the time-variant value and confirming that the identity of the receiving party 710 is correct. The requesting party 720 can then retrieve the random key and decrypt the portion of the $Token_{AB}$ that was encrypted using the random key. The requesting party 720 verifies the time-variant value included therein.

The requesting party 720 then generates a token $Token_{BA}$ to be encrypted using the random key and sent to the receiving party 710 at step 764. $Token_{BA}$ can include at least a time-variant value and other information to allow the receiving party 710 confirm that the requesting party 720 is capable of encrypting and decrypting messages using the random key. As embodied herein, the time-variant values can include random values (e.g., RCR, SCR) as appropriate. Additionally, the arrangement of the values in the tokens can vary according to a pre-established scheme to further increase the difficulty of malicious third parties attempting to intercept and interpret the messages and address replay of ciphertext.

As another example, and not by way of limitation, mutual authentication functions can implement a five-pass authentication in which the sensor 110 and data receiving device are authenticated by use of a trusted third party. The five-pass authentication can include a hybrid of the three-pass authentication and four-pass authentication. In particular, the sensor 110 can initiate the exchange and send a random value to the data receiving device. This message can be interpreted as an authentication request or can follow a separate authentication request in which, for example, the type of multi-pass authentication to be used is determined. The data receiving device can include the random value and an additional random value in a message to the trusted third party. The trusted third party can generate an encryption key based on the random values and provide it to the data receiving device. The data receiving device can provide the encryption key to the sensor 110 in a message encrypted using the encryption key. The data receiving device can also provide an additional random value generated by the data receiving device from which the sensor 110 can derive the encryption key. The sensor 110 can also send a confirmation message to the data receiving device to verify that it has received the encryption key appropriately.

Figure 7D:
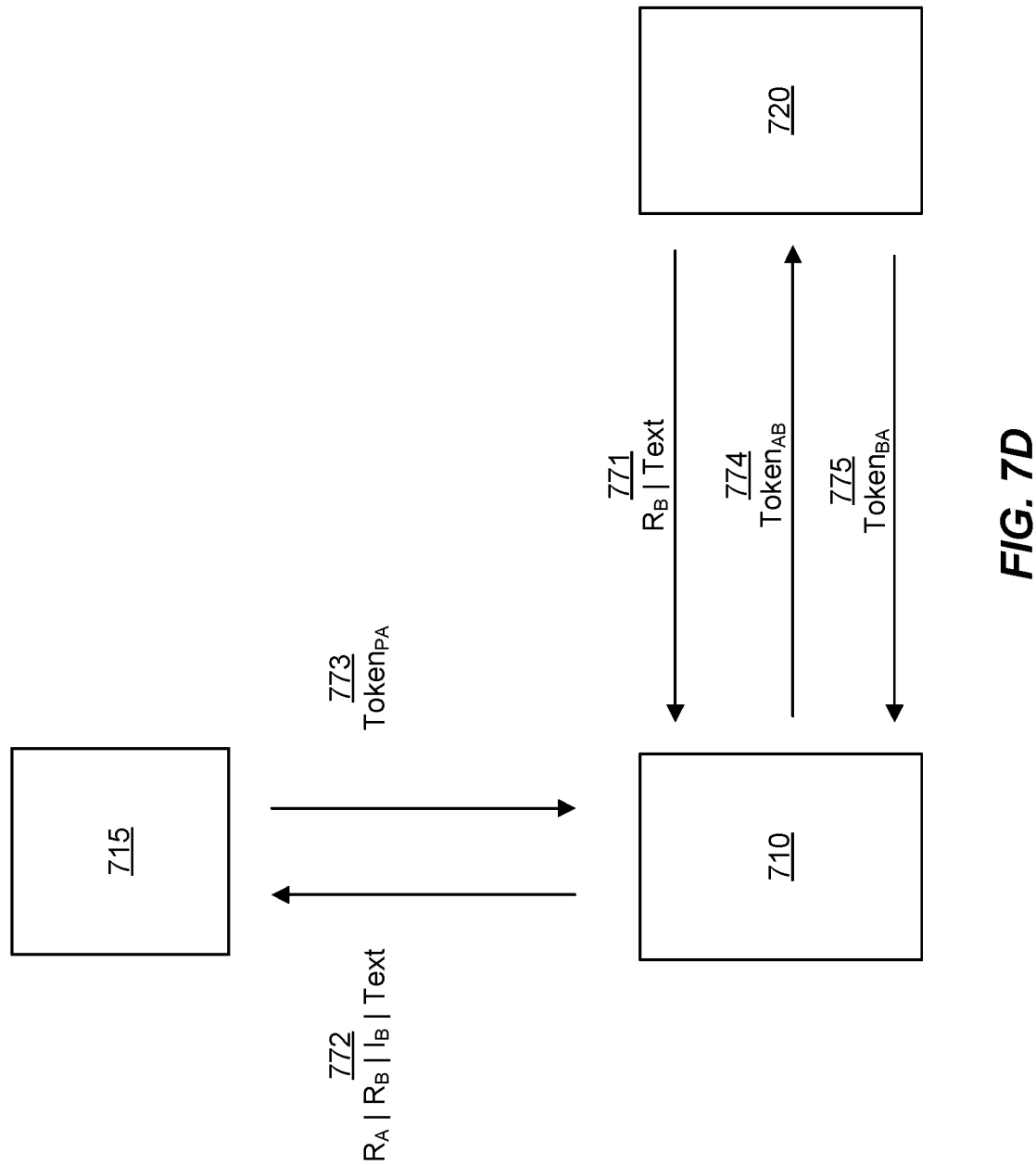

For purpose of illustration and not limitation, reference is made to the exemplary embodiment of a mutual authentication scheme for use with the disclosed subject matter as shown in FIG. 7D. The five-pass mutual authentication scheme will be described with respect to FIG. 7D. In the five-pass mutual authentication scheme, the authentication begins at step 771 with the requesting party 720 (e.g., at sensor 110) sending the receiving party (e.g., a data receiving device) a message including a random value $R_B$. The random value can take the form of plain-text challenge parameters, as embodied herein. As with the other mutual authentication schemes, the authentication can optionally begin with the requesting party 720 sending an express authentication request. The authentication request can be used to identify the type of authentication scheme that will be used, which can inform the requesting party 720 of whether it must provide additional information, such as the random value $R_B$ to the receiving party 710.

The receiving party 710 receives the random value $R_B$ and generates a request to the trusted third-party 715. The request can include at least new random value $R_A$, the random value $R_B$, an identifier for the requesting party 720 $I_B$ and optionally, text. At step 772, the receiving party 710 sends this message to the trusted third party 715. As embodied herein, the request can be sent in an encrypted fashion, e.g., using a key shared between the trusted third party 715 and the receiving party 710, or can optionally be sent in plain text as none of the values are expected to be sensitive. The trusted third party 715 can receive the message and generate a token $Token_{PA}$. $Token_{PA}$ is used to share a random key for use for communication between the requesting party 720 and the receiving party 710 based on the random values $R_A$ and $R_B$. $Token_{PA}$ is characterized by including two portions which are each encrypted using a separate key. A first encrypted portion is encrypted using a key shared between the trusted third-party 715 and the receiving party 710. The key can be derived from the random value $R_A$ to decrease the risk of compromised keys. The second encrypted portion is encrypted using a key shared between the trusted third party 715 and the requesting party 720 (e.g., the sensor 110). The key can be derived from the random value $R_B$ to decrease the risk of compromised keys. The first portion includes the random key, the random value $R_A$, an identifier for the requesting party 720, and text. The second portion includes the random value $R_B$, the random key, and an identifier for the receiving party 710. The trusted third party sends this token to the receiving party 710 at step 773.

Upon receipt of the $Token_{PA}$, the receiving party 710 decrypts the first portion of the $Token_{PA}$ and verifies its contents. The receiving party 710 can confirm that the random value $R_A$ is correct to ensure that the message is not a repeat of a previous response to a key-request message. The receiving party 710 can also confirm that the identity of the requesting party 720 is correct. The receiving party 710 can then construct a $Token_{AB}$ to be sent to the requesting party 720. The $Token_{AB}$ includes the encrypted second portion of the $Token_{PA}$ (still encrypted because the receiving party 710 does not have access to the key shared between the trusted third party and the requesting party 720), and another portion encrypted using the random key provided by the trusted third party. This other portion includes at least a new random value (e.g., a new challenge-response parameters) that can be used to confirm accuracy of the requesting party's decryption and the random value $R_B$, which can be used by the requesting party 720 as a challenge parameter to verify that the random key is to be used for the current communication session. At step 774, the receiving party 710 sends this $Token_{AB}$ to the requesting party 720. The requesting party 720 receives the token and first decrypts the portion encrypted using the key shared between the trusted third party 715 and the requesting party 720. The requesting party 720 verifies the information in the encrypted portion, by, for example, confirming the random value $R_B$ and confirming that the identity of the receiving party 710 is correct. The requesting party 720 can then retrieve the random key and decrypt the portion of the $Token_{AB}$ that was encrypted using the random key. The requesting party 720 verifies the random value $R_B$ included therein as well.

The requesting party 720 then generates a token $Token_{BA}$ to be encrypted using the random key and sent to the receiving party 710 at step 775. $Token_{BA}$ can include at least the new random value provided in $Token_{AB}$ and other information to allow the receiving party 710 confirm that the requesting party 720 is capable of encrypting and decrypting messages using the random key. The new random value then acts a challenge-response token, described herein. Additionally the arrangement of the values in the tokens can vary according to a pre-established scheme to further increase the difficulty of malicious third parties attempting to intercept and interpret the messages and address replay of ciphertext.

As embodied herein, authenticated commands can occur in the context of a mutual authentication exchange as described above. After completing a security challenge from the sensor 110, the data receiving device can issue an authenticated command or send an authenticated message in the form of an opcode in plain-text followed by an encrypted payload. The protocol for the encrypted payload can vary according to the command or to the value of the payload. As an example, in one format of the payload, the encrypted payload can include RCR, a command opcode, and SCR encrypted with the key SAK and the subsequent nonce derived from the synchronized nonce. SCR can be taken from the preceding mutual authentication exchange and can be regenerated for each command request. RCR can be newly generated and returned to the data receiving device in the reply to complete the authentication. If the sensor 110 determines that the authenticated command fails to follow the precise messaging protocol, the authenticated command can fail. In particular, the sensor 110 can optionally not acknowledge the request to avoid signal leakage. A response to an authenticated command can include a specified collection of data between SCR and RCR, with the payload encrypted with key SAK and the appropriate subsequent nonce of the nonce sent with the authenticated command.

As embodied herein, during manufacture, sensors 110 can be set to a post-manufacturing state by receiving an encryption initialization command message over a communication interface (e.g., an NFC interface incorporated in the ASIC 200 of the sensor 110). The encryption initialization command causes the sensor 110 to apply encryption and commit the encryption state to non-volatile memory. This action can also trigger an ASIC command to disable ports on the ASIC 200 for debugging and reprogramming and can further trigger a re-mapping of the general-purpose input/output (GPIO) pins.

As embodied herein, the dedicated data receiving device 120 can be similarly provided to end users in a firmware-locked state, with the internal program flash of the ASIC 200 of the dedicated data receiving device 120 shipped with debug and programming ports locked, preventing access without a mass erase. As such, the runnable image (including any long-term stored sensitive data) can be protected from tampering and view.

An NFC Initiation authenticated command can be sent when a data receiving device powers the sensor 110 with an NFC scan to function as a sensor activation command. This event can occur, for example, when the sensor 110 is activated by the data receiving device. Scan data can be protected by a session key (e.g., SEK). To initiate the NFC Initiation command, upon a successful challenge authentication, the sensor 110 can send the sensor secret (SS) to the data receiving device. The data receiving device can use SS to derive the session key (SEK). Subsequently, SEK can be used by the sensor 110 and data receiving device as the key to a cipher with an appropriate nonce and, for example, a block number as the counter. Under this architecture, only an authenticated sensor 110 and data receiving device should be provided knowledge of SEK.

Additional authenticated commands can be used to cause the sensor 110 to perform additional functions. As an example, an authenticated Request Information command can be an authenticated command to cause the sensor 110 to determine and return parameters used by the data receiving device to derive SEK.

As another example, a Communication Initialization authenticated command can be used to cause the sensor 110 to enable components of the sensor 110 related to one or more functions of the communication module 240. As an example, to preserve security and battery life, sensors 110 can optionally not be delivered to users with certain communication functions (e.g., BLE) enabled. The communication functions can be enabled once the sensor 110 is activated, as appropriate. As an example, BLE communications can be made available once a sensor 110 is activated by a dedicated data receiving device 120 or data receiving device. The Communication Initialization command can be issued separately from a sensor activation command or can be automatically triggered by the sensor 110 receiving the sensor activation command. The Communication Initialization command can return a hardware address and Binding ID ("BID") for later use during the connection session.

Figure 8:
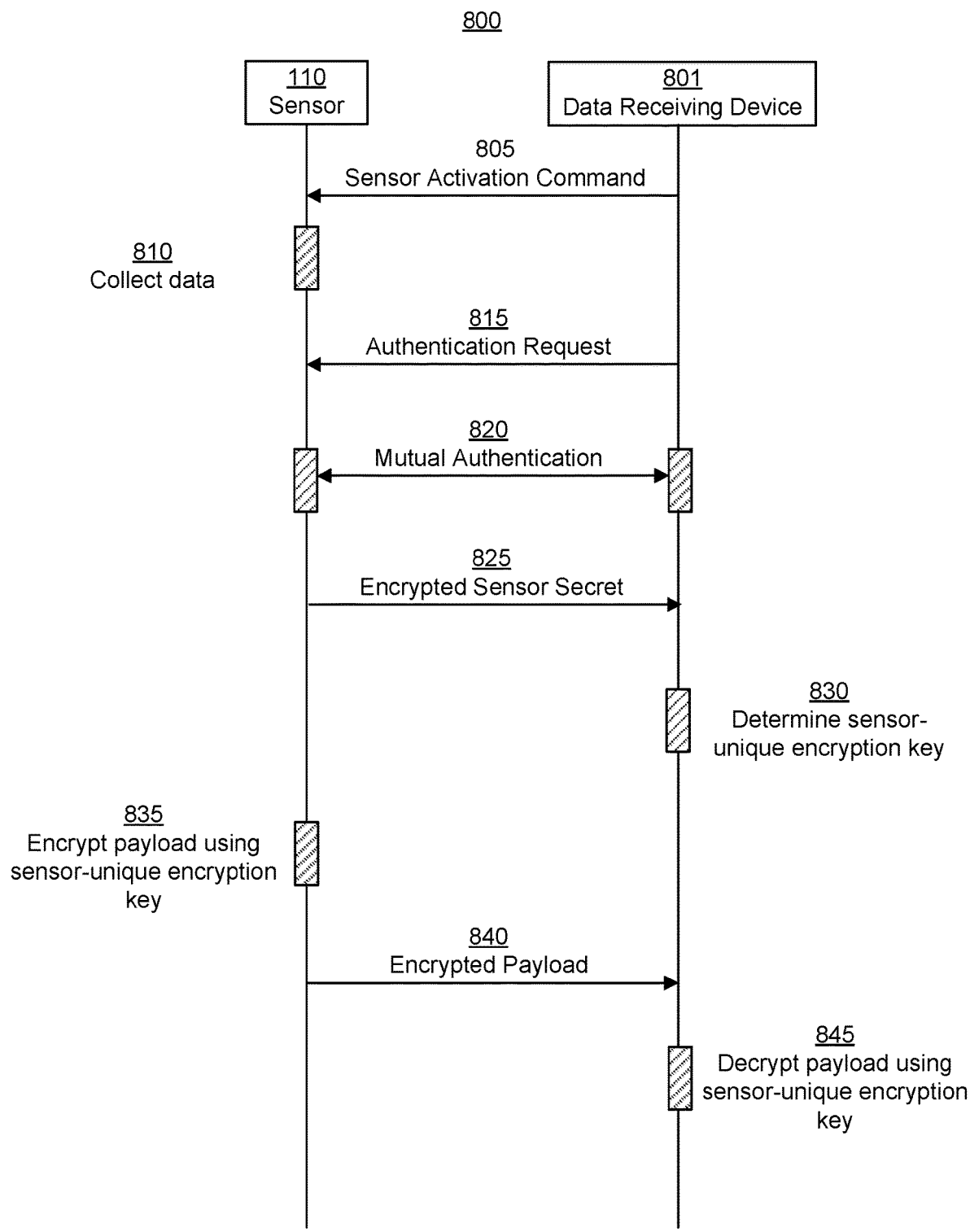
FIG. 8 is a diagram illustrating an example data flow for secure exchange of data between two devices according to the disclosed subject matter.

For purpose of illustration and not limitation, reference is made to the exemplary embodiment of a message sequence diagram 800 for use with the disclosed subject matter as shown in FIG. 8. FIG. 8 illustrates a message sequence diagram 800 that demonstrates an example exchange of data between a pair of devices, particularly a sensor 110 and a data receiving device 801. The data receiving device 801 can, as embodied herein, be a dedicated data receiving device 120 or a multi-purpose data receiving device 130. At step 805, the data receiving device 801 can transmit a sensor activation command 805 to the sensor 110, for example via a short-range communication protocol compatible with the sensor 110. The sensor 110 can, prior to step 805 be in a primarily dormant state, preserving its battery until full activation is needed. After activation during step 810, the sensor 110 can collect data or perform other operations as appropriate to the medical hardware 260 of the sensor 110. Although step 810 is shown as only occurring once during the exchange of data, as embodied herein, step 810 can be performed continuously by the sensor 110 as appropriate to the medical hardware 860.

At some point after step 810 first occurs, at step 815 the data receiving device 801 can initiate an authentication request command 815. In response to the authentication request command 815, both the sensor 110 and data receiving device 801 can engage in a mutual authentication process 820. For example, the sensor 110 and data receiving device 801 can perform a mutual authentication process, such as those illustrated with respect to FIGS. 7A-7D and described herein. The mutual authentication process 820 can involve the transfer of data, including challenge parameters that allow the sensor 110 and data receiving device 801 to ensure that the other device is sufficiently capable of adhering to the security framework described herein. For example, the mutual authentication process can involve the data receiving device 801 deriving a sensor-unique authentication key (e.g., SAK) based on sensor-unique and random values provided by the sensor 110 to the data receiving device 801.

Following a successful mutual authentication process 820, at step 825 the sensor 110 can provide the data receiving device 801 with a sensor secret 825 (e.g., SS). The sensor secret can likewise contain sensor-unique values and be derived from random values generated during manufacture. The sensor secret can be encrypted prior to or during transmission to prevent third-parties from accessing the secret. As embodied herein, the values used to derive the sensor secret can be universally unique, so that the sensor is unique to the communication session between the sensor 110 and the data receiving device 801. As embodied herein, the sensor secret 825 can be encrypted via one or more of the keys generated by or in response to the mutual authentication process 820. At step 830, the data receiving device 801 can derive a sensor-unique encryption key (e.g., SEK) from the sensor secret. As embodied herein, the sensor-unique encryption key can further be session-unique, as described herein. As such, the sensor-unique encryption key can be determined by each device without being transmitted between the sensor 110 or data receiving device 801, ensuring that only devices with access to the root keys, communication protocols, and secret information is capable of decrypting data encrypted by the sensor-unique encryption key.

At step 835, the sensor 110 can encrypt data to be included in payload. As appropriate, the data can include sensitive medical data, including biometric data or results of medicant delivery attempts. At step 840, the sensor 110 can transmit the encrypted payload 840 to the data receiving device 801 using the communication link established between the appropriate communication models of the sensor 110 and data receiving device 801. At step 845, the data receiving device 801 can decrypt the payload using the sensor-unique encryption key derived during step 830. Following step 845, the sensor 110 can deliver additional (including newly collected) data and the data receiving device 801 can process the received data appropriately. As embodied herein, the data receiving device 801 can further send data to the sensor 110 encrypted using the sensor-unique encryption key derived during step 830. The sensor 110 can decrypt the data using the sensor-unique encryption key stored in the storage 230 of the ASIC 200.

Embodiments described herein can repeat one or more steps of the method of FIG. 8, where appropriate. Although this disclosure describes and illustrates particular steps of the method of FIG. 8 as occurring in a particular order, this disclosure contemplates any suitable steps of the method of FIG. 8 occurring in any suitable order. Moreover, although this disclosure describes and illustrates an example method for encrypting and transmitting sensitive medical data including the particular steps of the method of FIG. 8, this disclosure contemplates any suitable method for encrypting and transmitting sensitive medical data including any suitable steps, which can include all, some, or none of the steps of the method of FIG. 8, where appropriate. Furthermore, although this disclosure describes and illustrates particular components, devices, or systems carrying out particular steps of the method of FIG. 8, this disclosure contemplates any suitable combination of any suitable components, devices, or systems carrying out any suitable steps of the method of FIG. 8.

As embodied herein, the dedicated data receiving device 120 can be configured to respond to requests from a user computing device 140, and in particular a proprietary application executing on the user computing device 140 with either plain-text or encrypted responses. Responses eliciting plain-text response include commands that do not involve authentication. As an example only and not by way of limitation, a non-authenticated command can include a command to request values that can be used to identify the dedicated data receiving device 120 or the user of the dedicated data receiving device 120 in order to establish an encrypted connection. As an example, the dedicated data receiving device 120 can respond to such a command from the user computing device 140 with information such as a reader UID, software version, firmware version, user personalization values, tokenized user identification, etc. Encrypted responses can be protected by, for example, a reader-unique derived key equivalent to SAK or SEK or a reader-unique random key. The dedicated data receiving device 120 can also use a transformation function that transforms authentication nonces into unpredictable sequences, e.g., unpredictable to those without access to the function, rather than monotonically increasing. As embodied herein, the reader can employ different keys than the keys used with a sensor, which can reduce the risk of compromise or specific attacks where a malicious actor obtains a sensor-unique key and attacks to use that key to validate exchanges between the dedicated data receiving device 120 and user computing device 140.

As discussed herein, the sensor 110 can be a device with restricted processing power, battery supply, and storage. The encryption techniques used by the sensor 110 (e.g., the cipher algorithm or the choice of implementation of the algorithm) can be selected based at least in part on these restrictions. The dedicated data receiving device 120 can be a more powerful device with fewer restrictions of this nature. Therefore, the dedicated data receiving device 120 can employ more sophisticated, computationally intense encryption techniques, such as cipher algorithms and implementations. For example, where a sensor 110 implements a lightweight block cipher a dedicated data receiving device 120 can implement a more complex cipher. Thus, the communication between the dedicated data receiving device 120 and the user computing device 140 can be considered more secure based on the advanced level of encryption used. This accords with the amount of data transmitted, as the dedicated data receiving device 120 can store and transmit greater amounts of sensitive medical data to the user computing device 140 than the sensor 110 would be capable of storing and transmitting. This also provides a benefit of enforcing greater levels of encryption with sensitive medical data as the data is transmitted farther from the sensor 110 and is at greater risk of interception or exposure.

As embodied herein, authenticated commands can involve the command request to follow a specified format, where the values for the format are synchronized from a prior exchange. Thus, the interface between the dedicated data receiving device 120 and the user computing device 140 can follow a similar procedure as that described for the interface between the sensor 110 and the dedicated data receiving device 120. This procedure can be used to reduce the impact of randomized probing attempts from third parties. The authenticated command format can be retained as proprietary information available only to a manufacturer 160 or service provider. As embodied herein, the authenticated command format can adhere to or be based on security protocols for securely transmitting data over wired or wireless communication links. As embodied herein, prior to issuing an authenticated command request, the dedicated data receiving device 120 and user computing device 140 can first synchronize values for exchange challenges and to synchronize an initial nonce.

As embodied herein, challenge random values can be sourced from a true random value generator function provided by, for example, a communication module or interface of the dedicated data receiving device 120 or user computing device 140. The user computing device 140 can further connect to a wide area network to retrieve true random values from a security provider. As embodied herein, the security challenges can be exchanged as unique payloads and can be saved in persistent memory for later use as an authentication parameter when sending or verifying authenticated commands.

The authentication scheme can take advantage of security features supported by the particular communication link between the dedicated data receiving device 120 and the user computing device 140. As an example, the dedicated data receiving device 120 and the user computing device 140 can be connected through a wired connection (e.g., USB) or wireless connection (e.g., Bluetooth, NFC, Wi-Fi, etc.). As embodied herein, these connections can be associated with particular device interfaces associated with particular device drivers. These device drivers can be managed by a trusted third-party or can be managed by a manufacturer and provider of the dedicated data receiving device 120 and proprietary application executing on the user computing device 140. As embodied herein, the encryption keys used by the user computing device 140 and dedicated data receiving device 120 can be supplied by updates to the device drivers or can be derived from information updated to the device drivers. The updated keys can be propagated to the dedicated data receiving device 120 from the user computing device 140 through secured device updates. The keys can be updated frequently through such program updates to reduce the risk of compromise from using pre-existing keys.

As described previously, the multi-purpose data receiving device 130 or the user computing device 140 can communicate with a remote cloud server 150. The devices can exchange various types of information including, but not limited to, sensitive medical data, statistical analysis regarding the medical data, alerts and recommendations, device software and firmware updates, updates regarding the security architecture (e.g., updates to authentication keys used and supported by the various devices). For simplicity, the following discussion refers to the user computing device 140, or a proprietary application executing on the user computing device 140, exchanging data with the remote cloud server 150. It should be understood that embodiments describing functions of the user computing device 140 can be adapted for use with a multi-purpose data receiving device 130. Furthermore, as embodied herein the upload of sensitive data to a remote cloud server 150 can be managed and controlled by a user. For example, a user can set privacy settings to restrict the volume and nature of data transmitted to the remote cloud server 150 for analysis. Additionally, the user computing device 140 can be configured to perform some or all of the advanced analytical functions of the remote cloud server 150 without access to a wide area network. The user can avoid accessing the remote cloud server 150 while having access to the same level of analysis and data collection as those users who choose to engage with the remote cloud server 150.

The general characteristics of the remote cloud server interface can be broadly similar to the other device interfaces described herein with respect to the security architecture. As an example, the user computing device 140 can be configured to respond to requests from a remote cloud server 150 with either plain-text or encrypted responses. Relatedly, communication between the remote cloud server 150 and the user computing device 140 can be bidirectional. Communication involving plain-text response can include commands that do not involve authentication. As an example only and not by way of limitation, a non-authenticated command can include a command to request values that can be used to identify the user computing device 120 or the user thereof in order to establish an encrypted connection. Encrypted responses can be protected by, for example, unique keys associated with the user or user-computing device equivalent to SAK or unique random keys. The user computing device 140 can also employ different keys than the keys used with a sensor or reader, which can reduce the risk of compromise or specific attacks where a malicious actor obtains, for example, a sensor-unique key and attempts to use that key to validate exchanges between the dedicated data receiving device 120 and user computing device 140.

As compared to sensor 110 and dedicated data receiving device 120, the multi-purpose data receiving device 130 and user computing device 140 can have no comparative restrictions to available processing power, battery supply, and storage. Therefore, the multi-purpose data receiving device 130 and user computing device 140 can be configured to employ significantly more complex encryption ciphers and authentication techniques, such as complex cipher algorithms and implementations. Thus, the communication between the multi-purpose data receiving device 130 and the remote cloud server 150 or the user computing device 140 and the remote cloud server 150 can be considered more secure based on the advanced level of encryption used. Moreover, this accords with the amount and nature of data transmitted, as the user computing device 140 can act in many ways as a repository of the sensitive medical data of the patient 170 and transmit large amounts (possibly including all) of the sensitive medical data collected about a patient 170. This also provides a benefit of enforcing greater levels of encryption with sensitive medical data as the data is transmitted farther from the sensor 110 and data receiving devices and is at greater risk of interception or exposure. Several stages of encryption can be used, with a mixture of proprietary and industry-standard encryption algorithms and architectures to protect sensitive medical data in storage and in transit. As an example, the sensitive medical data can be encrypted prior to or during transmission between multi-purpose data receiving device 130 and the remote cloud server 150 or the user computing device 140 and the remote cloud server 150 using mutually-agreed encryption keys (e.g., determined using a mutual authentication scheme as described herein). The packets of the encrypted payload can further be delivered via secured transfer protocols, including, but not limited to HTTPS, SFTP, FTPS, SSL, SSH, etc. The credentials for establishing the connections via secured transfer protocols can be further based on session-, device-, or -user-unique keys similar to those described herein.

As embodied herein, communication links between the user computing device 140 and the cloud server 150 can be associated with particular device interfaces associated with particular device drivers. These device drivers can be managed by a trusted third-party or can be managed by a manufacturer and provider of the low-power medical monitoring system 100. As an example, the provider can generate secured drivers to facilitate the establishment of communication links. The secured drivers can be tied to software and version updates so that the remote cloud server 150 can only communicate with a user computing device 140 that has drivers (and encryption keys) updated to the appropriate software version level. In this manner, the low-power medical monitoring system can ensure that keys which may have been discovered or compromised over time cannot be used to compromise the system at large. The updated keys can be propagated to the user computing device 140 from the remote cloud server 150 or from the provider of the proprietary application through secured device updates. The keys can be updated frequently through such program updates to reduce the risk of compromise from using pre-existing keys.

As embodied herein, the user computing device 140 or multi-purpose data receiving device 130 can be configured to operate in a pass-through manner in which the data received via secured communication with a sensor 110 or a dedicated data receiving device 120 is not decrypted on the user computing device 140 or multi-purpose data receiving device 130. As an example, the multi-purpose data receiving device 130 can act merely as a method for a sensor 110, which does not have the ability to connect to a wide area network, to send data to the remote cloud server 150. The multi-purpose data receiving device 130 can operate without even knowing the key used to the encrypt the sensitive medical data. In such cases, the key (e.g., SEK) can be known by the sensor 110 and the remote cloud server 150, while a separate key (e.g., SAK) can be used to validate the multi-purpose data receiving device 130 can communicate with the sensor 110 and can also communicate with the remote cloud server 150 on behalf of the sensor 110.

Figure 9:
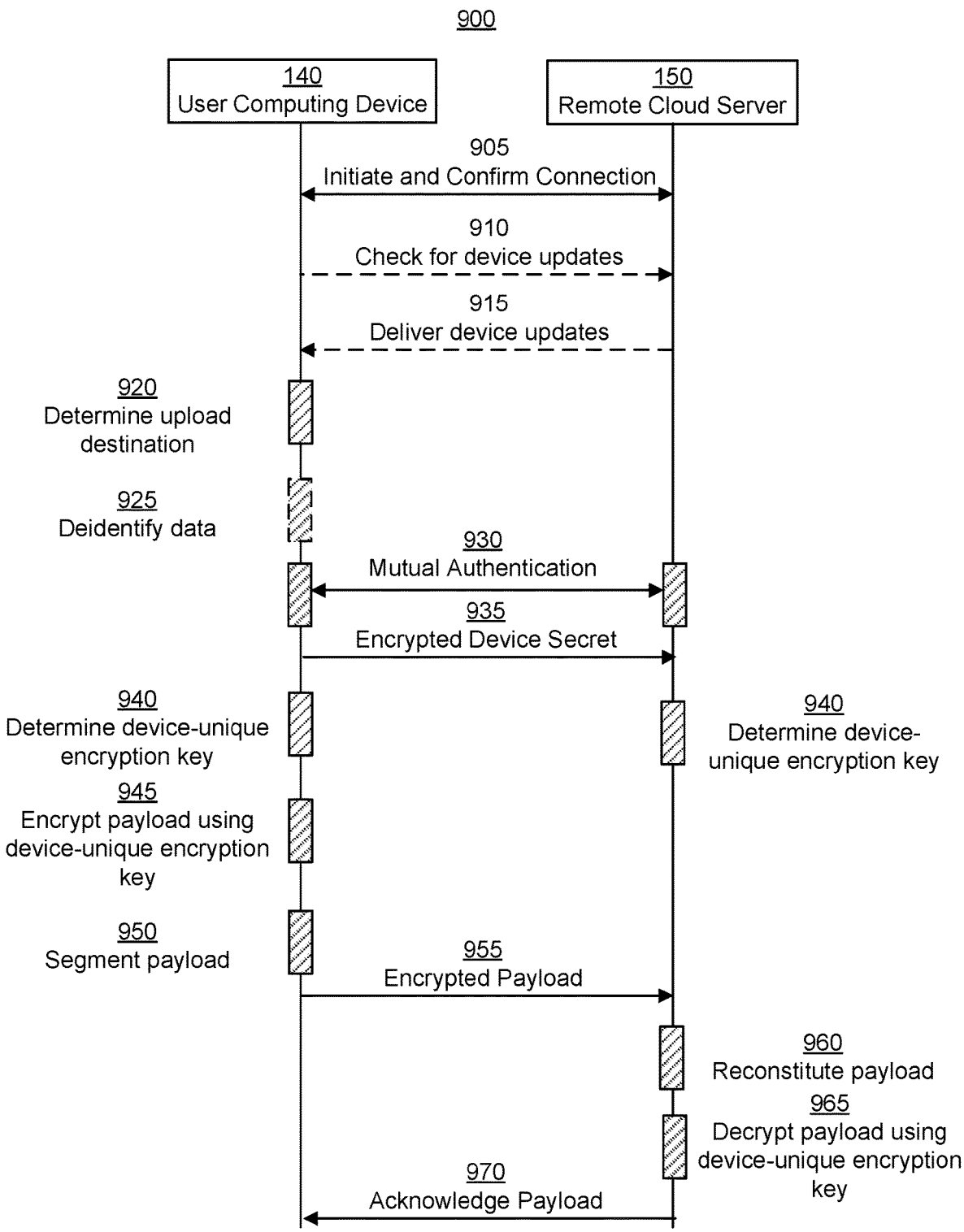
FIG. 9 is a diagram illustrating an example data flow for secure exchange of data between two devices according to the disclosed subject matter.

For purpose of illustration and not limitation, reference is made to the exemplary embodiment of a message sequence diagram 900 for use with the disclosed subject matter as shown in FIG. 9. FIG. 9 illustrates a message sequence diagram 900 that demonstrates an example exchange of data between a pair of devices, particularly a user computing device 140 and a remote cloud server 150. As embodied herein, the multi-purpose data receiving device 130 can be configured to perform many or all of the functions of the proprietary application executing on the user computing device 150 as described herein. Thus, FIG. 9 can also serve to illustrate the message sequence diagram for data exchanged between a multi-purpose data receiving device 130 and a cloud server 150.

At step 905, the user computing device 140 can attempt to initiate a connection with the remote cloud server 150. The user computing device 140 can send a request and receive an acknowledgement from the remote cloud server 150 indicating that a connection is available, or that a preliminary connection has been successfully established. As embodied herein, this connection can be made using one or more conventionally-secured communication protocols (e.g., HTTPS, TLS/SSL, SFTP, etc.) or can be made using a less secure, but more efficient communication protocol. In light of a desire for heightened security for the sensitive medical data collected by the user computing device 140, the user computing device 140 and remote cloud server 150 can undertake a sequence of steps to appropriately secure, encrypt, and transmit the sensitive data. As embodied herein, if the user computing device 140 is unable to establish a connection with the remote cloud 150, it can continue at regular intervals to attempt to establish a connection (e.g., ever 1 second, 10 seconds, 60 seconds, etc.). While attempting to establish a connection, the user computing device 140 can secure the collected data for longer term storage. For example, the user computing device 140 can be instructed to retain data at a highly granular level and avoid destroying data or summarizing data without granular backups until the data can be confirm as having been uploaded to the remote cloud device 150. The user computing device 140 can warn a user of storage capacity approaching full utilization and potentially encourage the user to provide for additional storage capabilities while the user computing device 140 attempts to ensure that a connection can be made.

At step 910, once the user computing device 140 is able to confirm a connection to the remote cloud server 150, the user computing device 910 can be configured to check for device updates to be delivered by the remote cloud server 150. For example, the remote cloud server 150 can deliver security updates to the user computing device 140 before the user computing device 140 can upload data to the remote cloud server. The remote cloud server 150 can further provide device updates (e.g., software updates, firmware updates) that are to be provided to other devices in the low-power medical monitoring system 100. For example, the remote cloud server 150 can pass device updates that are to be installed to a dedicated data receiving device 120 which the user computing device 140 can communicate with in the past.

At step 915, the remote cloud server 150 can deliver any appropriate device updates. The user computing device 140 can install those updates as needed, after verifying the integrity of the device updates with, for example, manufacturer-supplied authentication and integrity check keys.

In addition to checking for device updates, the user computing device 140 can be configured to request the remote cloud server 150 for other notifications and updates. As an example, the user computing device 140 can check in with the remote cloud server 150 for message for the user. The message can include, for example, updates about the sensitive medical data processed by the remote cloud server 150, updates summarizing results from data mining performed by the remote cloud server 150 as described herein, news and product information about the low-power medical monitoring system, etc. The remote cloud server 150 can deliver the notifications to the user computing device 140 to be displayed to a user.

At step 920, the user computing device 140 can determine an upload destination for the data. As an example, the low-power medical monitoring system 100 can provide for a variety of destinations to which data can be uploaded depending on, for example, the identity of the patient or user computing device 140, the location of the patient or user computing device 140, the intended use for the data, etc. As an example, the patient can be in a jurisdiction with data privacy controls that mandate that only remote cloud servers 150 which a specific geographic location can be used for sensitive medical data. The user computing device 140 (or optionally the remote cloud server 150) can determine which destination is appropriate for the data. As another example, the user computing device 140 (or optionally the remote cloud server 150) can determine a remote cloud server 150 that is likely to provide for a faster, more stable upload of the sensitive medical data. As yet another example, the low-power medical monitoring system 100 can contain remote cloud servers that support the collection of large-scale public data in addition to individualized personal medical data. The low-power medical monitoring system 100 can provide for such collection to support public health efforts, provide application support to users (e.g., to identify and determine errors with devices), provide large-scale analysis for patients, etc.

Based on the selection of the upload destination, the user computing device 140 can perform step 925 in which the user computing device 140 determines the nature of the data to be transmitted and can deidentify or anonymize the data. The data to be included in an upload can include data collected live (e.g., data recently received from a sensor 110) and can include historical data associated with a patient 140. As an example, the user computing device 140 can be configured to collect data continuously or over short periods of time to ensure that data collected about a patient is fresh and accurate. However, the user computing device 140 can be configured to package that data into larger chunks prior to uploading that the data to the remote cloud server 150. For example, individual readings related to blood glucose level monitoring can be relatively small. The amount of data exchanged during the procedures to establish and maintain a connection can be larger than the size of an individual reading. Thus, it can be inefficient for the user computing device 140 to upload each reading as it arrives. The user computing device 140 can package the data for transmission based on the size of a target payload (e.g., a file size, number of readings etc.), a time associated with the readings (e.g., covering a target period of time), a time since data was last uploaded, etc.

For example, the user computing device 140 can strip the data of any personally identifying information of the patient from which the data was collected. The user computing device 140 can also remove information that can be used to determine a particular individual (e.g., the identity of a specific dedicated data receiving device 120 used to collect the data). By anonymizing the data, the low-power medical monitoring system can be understood to be supporting efforts of patient privacy and confidentiality while also supporting programs that rely on such anonymous data for research and public health decisions. After de-identifying the data the user computing device 140 can merely upload the collected data to the remote cloud server 150 using the connection that has been established.

As embodied herein, the user computing device 140 can continue to follow the process outlined in the message flow 900 as a way of performing under the security architecture. Additionally, although described as being performed by the user computing device 140, sensitive medical data can be de-identified by other devices in the low-power medical monitoring system, such as a dedicated data receiving device 120 or multi-purpose data receiving device 130, prior to the data being sent to the user computing device 140, or by the remote cloud server 150 after the data has been sent by the user computing device 140.

At step 930, the user computing device 140 and remote cloud server 150 can perform a mutual authentication exchange, e.g., the mutual authentication exchange described herein, to validate that the devices are able to access and process the same root keys and other security key information. As embodied herein, the root keys and device-specific keys used for this exchange can vary from the root keys and device-specific keys used for exchanges between a sensor 110 and multi-purpose data receiving device 130 or dedicated data receiving device 120 and user computing device 140, etc. At step 935, the user computing device 140 can transmit a device secret 935 to the remote cloud server 150, the device secret can form part of the information used to derive the device-unique encryption key that forms a basis for the encryption cipher that will be used while transmitting a payload including the sensitive medical data. As embodied herein, the device secret can contain random values that ensure that the particular device secret that is transmitted at 935 is unique to the communication session between the user computing device 140 and the remote cloud server 150. The device secret can be encrypted prior to or during transmission to prevent third-parties from accessing the secret. At step 940, the remote cloud server 150 and user computing device 140 can derive the device-unique encryption key.

As embodied herein, the mutual authentication process or procedure described herein for determining device-unique encryption keys can also allow both the user computing device 140 and remote cloud server 150 to establish a unique correspondence between a particular authentication or encryption key and the device that derived it. For example, the user computing device 140 and remote cloud server 150 can each associate the keys used for communication with the other device with that device so that, at some later point in the communication, the devices can verify that data encrypted using the device-unique encryption key (or data otherwise sent by the other device) was encrypted by correct device. In so doing, the security protocol described herein can be used to avoid so-called "man in the middle attacks" where a third-party obtains credentials involved in transmitting data and attempts to use those credentials as though they should be associated with the third-party. By performing "certificate pinning" using, for example, the authentication keys used during the mutual authentication or the device-unique encryption key, the user computing device 140 and remote cloud server 150 can each independently verify that no other party has intercepted any data packets sent between the two devices.

At step 945 the user computing device 140 can encrypt a payload including the sensitive medical data (e.g., medical data including personally identifying information for the patient) using the device-unique encryption key. As described previously, because the user computing device 140 has access to greater stores of computing power, the user computing device 140 can use a more complex encryption cipher than the encryption cipher that can be used by less powerful devices in the low-power medical device monitoring system.

During the course of normal operation of the low-power medical monitoring system 100 an individual reading can be subject to multiple rounds of encryption and decryption as the data is transmitted from sensor 110 to dedicated data receiving device 120 to user computing device 140 to remote cloud server 150, with each step potentially using different keys and using increasingly complex levels of encryption. For example, when transmitting a reading from a sensor 110 to a dedicated data receiving device 120, the reading can be encrypted using a light-weight cipher based on a sensor-unique key. The dedicated data receiving device 120 can then decrypt the reading, repackage it, and re-encrypt it using a more complex cipher based on a reader-unique key before it is transmitted to the user-computing device 140. Similarly, the user computing device 140 can decrypt the reading, repackage it, and re-encrypt it using an even more complex cipher based on a device-unique key before it is transmitted to the remote cloud server. At each stage, the reading can be encrypted and decrypted so that encryption keys need not be shared between device complexity (and durability levels). In this manner, if, for example, a sensor-unique key is compromised, other keys, such as a user computing device key remain unaffected. Increasingly complex ciphers can also be used because the respective devices will have more available computing resources and power. As described herein, at particular stages, the data can optionally not be decrypted and re-encrypted and be passed through to another level of device.

At step 950, the user computing device 140 can segment the payload into a plurality of transmission packets. The user computing device 140 can optionally segment the payload prior to encrypting the payload using the device-unique encryption key. The user computing device 140 can thus encrypt each of the payload segments using device-unique encryption key. As embodied herein, it can be advantageous for the user computing device 140 to segment the payload into packets prior to transmission. Packetizing the payload can improve the stability of communications with the remote cloud server 150 as the system can more easily recover data that is lost in transmission without having to transmit the entire remainder of the payload. Such a protocol can include additional integrity checks to verify that individual packets have been received by the remote cloud server 150. Additionally, though not illustrated, the remote cloud server 150 can send periodic acknowledgements of packets that have been received so that the user computing device 140 can efficiently begin retransmission procedures as needed. Additionally, the user computing device 140 can apply any suitable compression techniques to the data of the payload to minimize the file size of the data that must be transmitted.

At step 955, the user computing device 140 sends the encrypted payload to the remote computing device 140. As described herein the user computing device 140 can transmit the data using one of any suitable communication protocols (e.g., HTTPS, SFTP, FTPS, SSL, etc.) that provide individual packet protection to the payload in additional to the block cipher applied to the payload prior to the initiation of the transmission. By using communication protocols that provide such protection, the user computing device 140 can further support protection for the data as the nature of the data will be further obscured from third-parties. As embodied herein, the user computing device 140 and remote cloud server 150 can alternatively forgo the use of a cipher based on the device-unique encryption key and can instead rely on the chosen protocol that provides individual packet-level protection.

At step 960, the remote cloud server 150 receives and reconstitutes the payload 960 from the received data packets. The remote cloud server 150 can identify any packets lost in transmission and request they be resent by the user computing device 140. Reconstituting the payload 960 can include reassembling the payload from the collection of packets. At step 965, the remote cloud server 150 can decrypt the payload using the device-unique encryption key. The remote cloud server 150 can confirm successful receipt of the contents of the payload, e.g., through the use of checksums or other error detection codes. At step 970, the remote cloud server 150 can send an acknowledgement of the payload to the user computing device 140. The acknowledgement can include a message indicating that the sensitive medical data has been received. As embodied herein, the acknowledgement can also be encrypted and delivered using communication protocols that provide packet-level encryption. Alternatively, the acknowledgement can be sent unencrypted or in plain text, as the acknowledgement can optionally not include sensitive data.

Embodiments described herein can repeat one or more steps of the method of FIG. 9, where appropriate. Although this disclosure describes and illustrates particular steps of the method of FIG. 9 as occurring in a particular order, this disclosure contemplates any suitable steps of the method of FIG. 9 occurring in any suitable order. Moreover, although this disclosure describes and illustrates an example method for encrypting and transmitting sensitive medical data including the particular steps of the method of FIG. 9, this disclosure contemplates any suitable method for encrypting and transmitting sensitive medical data including any suitable steps, which can include all, some, or none of the steps of the method of FIG. 9, where appropriate. Furthermore, although this disclosure describes and illustrates particular components, devices, or systems carrying out particular steps of the method of FIG. 9, this disclosure contemplates any suitable combination of any suitable components, devices, or systems carrying out any suitable steps of the method of FIG. 9.

As described herein, to secure the transmission and storage of sensitive medical data in the low-power medical monitoring system 100, more complex cryptographic functions can be employed by devices further downstream from the sensor 110 that have comparatively fewer restrictions on processing power. For example, sensitive medical data can be encrypted by the sensor 110 prior to and during transmission between the sensor 110 and a dedicated data receiving device 120 using a first cryptographic function and based on a first cryptographic key. The first cryptographic function can be a lightweight cryptographic function (e.g., a lightweight block cipher or lightweight stream cipher) as described herein. Then, when sensitive medical data is transmitted to a user computing device 140, the sensitive medical data can be encrypted prior to and during transmission with the user computing device 140 using a second cryptographic function and based on a second cryptographic key. The second cryptographic function can be a more complex cryptographic function than the first cryptographic function. The second cryptographic key can be different from the first cryptographic key.

As another example, sensitive medical data can be encrypted by the sensor 110 prior to and during transmission between the sensor 110 and a multi-purpose data receiving device 130 using a first cryptographic function and based on a first cryptographic key. The first cryptographic function can be a lightweight cryptographic function (e.g., a lightweight block cipher or lightweight stream cipher) as described herein. When sensitive medical data is transmitted to a user computing device 140 or remote cloud server 150 by the multi-purpose data receiving device 130, the sensitive medical data can be encrypted prior to and during transmission using a second cryptographic function and based on a second cryptographic key. The second cryptographic function can be a more complex cryptographic function than the first cryptographic function, as described herein. The second cryptographic key can be different from the first cryptographic key. Additionally, or alternatively, the transmission of the sensitive medical data can be encrypted with packet-level encryption or other application-level, transport-level, or network-level encryption as appropriate to the communication medium and protocol chosen for the transmission.

Additionally or alternatively, as embodied herein, the user computing device 140 can use an even more complex cryptographic scheme when transmitting data to the remote cloud server 140. As an example, sensitive medical data can be encrypted by the sensor 110 prior to and during transmission between the sensor 110 and a dedicated data receiving device 120 or multi-purpose data receiving device 140 using a first cryptographic function and based on a first cryptographic key. The first cryptographic function can be a lightweight cryptographic function (e.g., a lightweight block cipher or lightweight stream cipher) as described herein. Then, when sensitive medical data is transmitted to a user computing device 140 by the dedicated data receiving device 120 or multi-purpose data receiving device 130, the sensitive medical data can be encrypted prior to and during transmission using a second cryptographic function and based on a second cryptographic key. The second cryptographic function can be a more complex cryptographic function than the first cryptographic function. The second cryptographic key can be different from the first cryptographic key. When the sensitive medical data is transmitted from the user computing device 140 to a remote cloud server 150, the sensitive medical data can be encrypted prior to and during transmission using a third cryptographic function and based on a third cryptographic key. The third cryptographic function can be a more complex cryptographic function than both the first cryptographic function and the second cryptographic function. The third cryptographic key can be different from both the first cryptographic key and second cryptographic key. Additionally, or alternatively, the transmission of the sensitive medical data from the user computing device 140 to the remote cloud server 150 can be encrypted with packet-level encryption or other application-level, transport-level, or network-level encryption as appropriate to the communication medium and protocol chosen for the transmission.

Following are examples of requests and included data that can be transmitted between the user computing device 140 and a remote cloud server. As embodied herein, the results and specification of requests can be formatted in a JSON or XML format, however it should be understood that any appropriate data packaging method can be used.

As described herein, upon initially connecting with the remote cloud server 150, the user computing device 140 can call an UpdateCheck function of the remote cloud server 150. The UpdateCheck function can cause the remote cloud server 150 to verify the current software or firmware versions in use and compare the current version with the version used by the user computing device (or other devices in the low-power medical monitoring system 150). The UpdateCheck function call can pass collected values to a suitable update comparison module associated with the remote cloud server 150. The UpdateCheck function call can include, by way of example and not limitation, values such as an application identifier and version number, an operating system identifier and version number, identifiers corresponding to the dedicated data-receiving device 120, multi-purpose data receiving device 130, or user computing device 140, descriptors for the operating environment of the dedicated data-receiving device 120, multi-purpose data receiving device 130, or user computing device 140, and a security token or security key.

As described herein, the user computing device 140 can determine to send anonymized or deidentified data to a data mining remote cloud server 150. The data mining server can collect data for the purposes of large-scale analysis for the low-power monitoring system provider or a variety of other sources. After deidentifying the data, the user computing device 140 can call a MiningDataUpload function of the remote cloud server 150. The MiningDataUpload function can cause the remote cloud server 150 to receive and process the deidentified data for use for data mining purposes. The MiningDataUpload function call can include, by way of example and not limitation, values such as device settings associated with the sensor 110 including a time since reset, firmware or software version, a lifetime count of the sensor 110, or nickname, a log of measurements including measured analyte values, food log entries, records associated with scheduled and unscheduled entries associated with analyte measurements such as time since initialization, activation, reset, or time change, measurement identifier, measurement timestamp, value of the analyte, trending values and directions associated with the analyte, and an indication of whether the measurement is actionable.

As embodied herein, the scheduled analyte entries can include time-stamped values corresponding to analyte measurements taken at a predetermined interval, such as 1-minute, 5-minute, or 15-minute intervals, or any other suitable interval. Additionally or alternatively, unscheduled analyte entries can include time-stamped values corresponding to analyte measurements taken in response to an input or condition, such as scanning of the sensor by the user, viewing of the dedicated data receiving device 120 or multi-purpose data receiving device 130 by the user, or a condition determined by the sensor.

The user computing device 140 can further call an UnencryptedDataUpload function of the remote cloud server 150. The UnencryptedDataUpload function can deliver a payload to the remote cloud server 150 that contains non-sensitive data. The UnenryptedDataUpload function call can include, by way of example and not limitation, values such as a device domain corresponding to the measured analytes or roles, a connection gateway identification, a user token, an identification of the a type of content included in the function all, a notification of the length of the provided content and/or the expected content.

A GetVersion call can include a UserToken. The UserToken can be encoded using any suitable encoding technique (e.g., Base64URL). The UserToken can include a header portion and a payload portion. The header portion can be decoded to identify the algorithm used to encode the payload. A receiving party (e.g., the remote cloud server 150) can decode the payload portion of the token using the identified algorithm to determine values including, but not limited to an token identification for the sensor 110 or user, user identifying information for the sensor 110 or user, such as the name, location, and preferred units of analytes.

The user computing device 140 can further call an EncryptedDataUpload function of the remote cloud server 150. The EncryptedDataUpload function can deliver a payload to the remote cloud server 150 that contains sensitive data. As embodied herein, the payload can include any or all of the payload data returned from the MiningDataUpload function, along with personal data about the user, including without limitation the particular sensor used by the user. As such, the device data that contains the sensitive data can be encrypted according to the procedures described herein. The EncryptedDataUpload function call can include values including, but not limited to, a data extraction timestamp, encoded data, a device identifier, diagnostic information, including an application version, activation time, initialization time, and operating system identification information, a drive identification, a driver key, a gateway and/or connection information, a device group identifier, a sensor time, a device serial number, and timestamp discrepancy check.

The user computing device 140 can further call a RetrieveData function of the remote cloud server 150. The RetrieveData function can send information to identify the device or patient. In return, the user computing device 140 can receive historical information about the data stored by the remote cloud server 150. As embodied herein, the RetrieveData function can be used to retrieve information uploaded from a first user computing device to be viewed at a second user computing device. The retrieve data function call and return information can include data including, but not limited to, a device identifier, a device type identifier, diagnostic information associated with the device, a data extraction time, device operating environment data, an identification of the most recent device to upload data for the user, an upload start time, a connection and/or gateway identifier, a user identifier, upload identifier, and upload route for each quantum of uploaded data.

In response to the RetrieveData function, the remote cloud server 150 can deliver a payload including the a listing of devices that have interacted with the sensor, along with additional data relating to the device usage history and/or data measured by or stored on the device. The listing of devices and data can include information such as, but not limited to, the creation data of data records, an identification, nickname, serial number or type associated with a device, the upload date of data uploaded from the device, timestamps associated with the data, analyte measurement counts associated with the data, food entry logs, counts associated with scheduled and unscheduled data collection events associated with each device, a user identifier, and a serial number associated with the device or user.

The user computing device 140 can further call a GetAnalyteHistory function of the remote cloud server 150. The GetAnalyteHistory function can retrieve data stored by the remote cloud server 150. The GetAnalyteHistory function can provide the stored information to be viewed on the user computing device 140. The data returned by the remote cloud server 150 can include by way of example and not limitation, identifiers of devices that have provided analyte data, the data of last upload by one or more of the devices and/or types of devices, raw analyte measurements, average analyte measurements, number of testing events recorded over a period of time, the range of analyte measurement values over a period of time, extrema values and other statistical measures (including quartile measurements) of the analyte measurements over a period of time, a data collection start date, a data collection end date, a data collection time range, and a count of events where the analyte was above or below a threshold value.

In addition to the specific embodiments stated and claimed below, the disclosed subject matter is also directed to other embodiments having any other possible combination of the dependent features claimed below and those disclosed above and in the attached figures. As such, the particular features disclosed herein can be combined with each other in other manners within the scope of the disclosed subject matter such that the disclosed subject matter should be recognized as also specifically directed to other embodiments having any other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

Embodiments disclosed herein include:

A. A method for secured communication between a medical sensor and a computing device comprising: receiving, by the medical sensor, an authentication request from the computing device; generating, based on values provided in the authentication request, a challenge-response message for the computing device; receiving, from the computing device, a responsive challenge-response message; verifying that the responsive challenge-response message comprises an expected value and corresponds to an expected format;

and in response to verifying the responsive challenge-response message, sending a sensor secret value to the computing device.

B. A method comprising: receiving, by a first computing device from a medical sensor, a sensor secret value; receiving, by a first computing device from the medical sensor, a set of encrypted medical readings created using a first cryptographic operation on unencrypted medical readings based on a first key derived from the sensor secret value, wherein the cryptographic operation comprises performing add-rotate-xor operations on the unencrypted medical data; deriving, by the first computing device, the first key based on the sensor secret value; and decrypting, by the first computing device, the set of medical readings using the derived first key with the cryptographic operation.

C. A method for secured communication between a medical sensor and a computing device comprising: receiving, by the medical sensor, an activation signal from the computing device through a short-range communication protocol; in response to the activation signal, verifying one or more authentication values associated with the computing device; and upon successfully verifying the authentication values associated with the computing device, collecting, by the medical sensor, sensor information from a patient.

D. A medical sensor arranged to provide secured communication with a computing device, the medical sensor comprising: means for receiving an authentication request from the computing device; means for generating, based on values provided in the authentication request, a challenge-response message for the computing device; means for receiving, from the computing device, a responsive challenge-response message; means for verifying that the responsive challenge-response message comprises an expected value and corresponds to an expected format; and means for sending, in response to verifying the responsive challenge-response message, a sensor secret value to the computing device.

E. A first computing device comprising: means for receiving from a medical sensor a sensor secret value; means for receiving from the medical sensor, a set of encrypted medical readings created using a first cryptographic operation on unencrypted medical readings based on a first key derived from the sensor secret value, wherein the cryptographic operation comprises performing add-rotate-xor operations on the unencrypted medical data; means for deriving the first key based on the sensor secret value; and means for decrypting the set of medical readings using the derived first key with the cryptographic operation.

F. A medical sensor arranged to provide secured communication with a computing device, the medical sensor comprising: means for receiving an activation signal from the computing device through a short-range communication protocol; means for verifying, in response to the activation signal, one or more authentication values associated with the computing device; and means for collecting sensor information from a patient, upon successfully verifying the authentication values associated with the computing device.

G. A computer program, computer program product or computer readable medium comprising instructions which, when executed by a computing device or a medical sensor, cause the computing device or the medical sensor to carry out the steps of the method of any of embodiments A, B, or C.

Each of embodiments A, B, C, D, E, F, and G may have one or more of the following additional elements in any combination: Element 1: wherein the sensor secret value comprises data unique to the medical sensor and one or more random values. Element 2: wherein the one or more random values are based on predefined values provided to the medical sensor, values generated by a communication module of the medical sensor, or values generated in response to user interactions. Element 3: further comprising: collecting, by the medical sensor, sensor information from a patient; and encrypting the sensor information using an encryption key derived from the sensor secret value. Element 4: further comprising sending the encrypted sensor information to the computing device using a short-range communication protocol. Element 5: wherein the sensor information comprises medical data about the patient. Element 6: wherein the medical data comprises body temperature, heart rate, blood glucose levels, or motion readings. Element 7: wherein encrypting the sensor information comprises encoding the sensor information with a power-efficient stream cipher or block cipher based on the encryption key. Element 8: further comprising: receiving, by the medical sensor, an activation signal from the computing device through a short-range communication protocol; in response to the activation signal, verifying one or more authentication values associated with the computing devices; and upon successfully verifying the authentication values associated with the computing device, collect, by the medical sensor, sensor information from a patient. Element 9: wherein the activations signal further delivers wireless power to one or more of the communication modules of the medical sensor. Element 10: wherein the medical sensor uses information received through the short-range communication protocol to establish a connection with the computing device over a second short-range communication protocol without requiring additional verification from the patient. Element 11: wherein the short-range communication protocol comprises Near-Field Communication and the second short-range communication protocol comprises Bluetooth Low Energy.

Element 12: wherein the add-rotate-xor operations comprise: segmenting the unencrypted medical readings into a series of data blocks; segmenting each data block into more than one words; and for each data block: rotating bits of a first word of the more than one words of the block by a first fixed amount; adding a second word of the more than one words of the block; performing a bitwise xor operation of the first key into the first word; rotating bits of the second word by a second fixed amount; and performing a bitwise xor operation of the first word into the second word. Element 13: further comprising: encrypting the decrypted medical readings using a second key and a second cryptographic function, wherein the second key comprises information unique to the first computing device and random values generated by the first computing device; and transmitting the encrypted medical readings to a second computing device. Element 14: wherein second cryptographic function is different from the first cryptographic function and is a more computationally-complex cryptographic function than the first cryptographic function. Element 15: wherein the encrypted medical readings are transmitted to second computing device via wired or wireless communication. Element 16: wherein the encrypted medical readings are transmitted using a packet-level-encoding computing protocol. Element 17: further comprising: decrypting, by the second computing device, the encrypted medical readings; and transmitting the decrypted medical readings to a third computing device after encrypting the medical readings with a third cryptographic function based on a third key, wherein the first key, the second key, and the third key are all different and are all derived from different root values and wherein the first cryptographic function, second cryptographic function, and third cryptographic function are all different. Element 18: wherein the sensor secret value comprises unique values associated with the medical sensor and random values generated by the medical sensor.

Element 19: wherein the activation signal further delivers wireless power to one or more communication modules of the medical sensor. Element 20: wherein the medical sensor uses information received through the short-range communication protocol to establish a connection with the computing device over a second short-range communication protocol without requiring additional verification from the patient. Element 21: wherein the short-range communication protocol comprises Near-Field Communication and the second short-range communication protocol comprises Bluetooth Low Energy.

Element 22: further comprising means for implementing the method according to any of elements 1 to 11.

Element 23: further comprising means for implementing the method according to any of elements 12 to 18.

Element 24: further comprising means for implementing the method according to any of elements 19 to 21.

By way of non-limiting example, example additions or combinations applicable to embodiment A include: Element 1 with any of Elements 2-11; Element 2 with any of Elements 1 and 3-11; Element 3 with any of Elements 1-2 and 4-11; Element 4 with any of Elements 1-3 and 5-11; Element 5 with any of Elements 1-4 and 6-11; Element 6 with any of Elements 1-5 and 7-11; Element 7 with any of Elements 1-6 and 8-11; Element 8 with any of Elements 1-7 and 9-11; Element 9 with any of Elements 1-8 and 10-11; Element 10 with any of Elements 1-9 and 11; Element 11 with any of Elements 1-10.

By way of non-limiting example, example additions or combinations applicable to embodiment B include: Element 12 with any of Elements 13-18; Element 13 with any of Elements 12 and 14-18; Element 14 with any of Elements 12-13 and 15-18; Element 15 with any of Elements 12-14 and 16-18; Element 16 with any of Elements 12-15 and 17-18; Element 17 with any of Elements 12-16 and 18; Element 18 with any of Elements 12-17.

By way of non-limiting example, example additions or combinations applicable to embodiment C include: Element 19 with any of Elements 20-21; Element 20 with any of Elements 19 and 21; Element 21 with any of Elements 19-20.

By way of non-limiting example, example additions or combinations applicable to embodiment D include: Element 22.

By way of non-limiting example, example additions or combinations applicable to embodiment E include: Element 23.

By way of non-limiting example, example additions or combinations applicable to embodiment F include: Element 24.

Additionally or alternatively, any of the elements and combinations applicable to embodiments A, B, C, D, E, F, and G are also applicable to any of the other elements and combinations applicable to embodiments A, B, C, D, E, F, and G.

What is claimed is:

1. A method comprising:
    receiving, by a first computing device from a sensor, a sensor secret value;
    receiving, by the first computing device from the sensor, a set of encrypted data created using a first cryptographic operation on unencrypted data based on a first key derived from the sensor secret value, wherein the first cryptographic operation comprises:
        segmenting the unencrypted data into a series of data blocks;
        segmenting each data block into more than one words; and
        for each data block, performing add-rotate-xor operations on the more than one words of the block, wherein the add-rotate-xor operations comprise:
            for each data block:
                rotating bits of a first word of the more than one words of the block by a first fixed amount;
                adding a second word of the more than one words of the block;
                performing a bitwise xor operation of the first key into the first word;
                rotating bits of the second word by a second fixed amount; and
                performing a bitwise xor operation of the first word into the second word;
    deriving, by the first computing device, the first key based on the sensor secret value; and
    decrypting, by the first computing device, the set of encrypted data using the derived first key with the first cryptographic operation.

2. The method of claim 1, further comprising:
    encrypting the decrypted data using a second key and a second cryptographic function, wherein the second key comprises information unique to the first computing device and random values generated by the first computing device; and
    transmitting the data encrypted using the second key to a second computing device.

3. The method of claim 2, wherein second cryptographic function is different from the first cryptographic function and is a more computationally-complex cryptographic function than the first cryptographic function.

4. The method of claim 2, wherein the data encrypted using the second key is transmitted to second computing device via wired or wireless communication.

5. The method of claim 2, wherein the data encrypted using the second key is transmitted using a packet-level-encoding computing protocol.

6. The method of claim 2, further comprising:
    decrypting, by the second computing device, the data encrypted using the second key; and
    transmitting the decrypted data previously encrypted using the second key to a third computing device after encrypting that data with a third cryptographic function based on a third key, wherein the first key, the second key, and the third key are all different and are all derived from different root values and wherein the first cryptographic function, second cryptographic function, and third cryptographic function are all different.

7. The method of claim 1, wherein the sensor secret value comprises unique values associated with the sensor and random values generated by the sensor.

* * * * *